(12) United States Patent
Grudic et al.

(10) Patent No.: US 11,389,069 B2
(45) Date of Patent: *Jul. 19, 2022

(54) HEMODYNAMIC RESERVE MONITOR AND HEMODIALYSIS CONTROL

(71) Applicants: Flashback Technologies, Inc., Boulder, CO (US); The Regents of the University of Colorado, Denver, CO (US)

(72) Inventors: Gregory Zlatko Grudic, Niwot, CO (US); Steven L. Moulton, Littleton, CO (US); Isobel Jane Mulligan, Niwot, CO (US)

(73) Assignees: Flashback Technologies, Inc., Westfield, NJ (US); The Regents of the University of Colorado, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/649,411

(22) Filed: Jul. 13, 2017

(65) Prior Publication Data
US 2017/0303799 A1    Oct. 26, 2017

Related U.S. Application Data

(63) Continuation of application No. 13/554,483, filed on Jul. 20, 2012, now Pat. No. 9,757,041.
(Continued)

(51) Int. Cl.
*A61B 5/02*    (2006.01)
*A61B 5/021*    (2006.01)
(Continued)

(52) U.S. Cl.
CPC ......... *A61B 5/02028* (2013.01); *A61B 5/021* (2013.01); *A61B 5/02042* (2013.01);
(Continued)

(58) Field of Classification Search
CPC ............. A61B 5/02028; A61B 5/7275; A61B 5/02042; A61B 5/4875; A61M 5/168
See application file for complete search history.

(56) References Cited

U.S. PATENT DOCUMENTS

| 4,930,517 A | 6/1990 | Cohen et al. |
| 5,074,310 A | 12/1991 | Mick |

(Continued)

FOREIGN PATENT DOCUMENTS

| CA | 2871608 | 2/2021 |
| EP | 2356579 | 5/2015 |

(Continued)

OTHER PUBLICATIONS

International Search Report and Written Opinion prepared by the U.S. Patent and Trademark Office as International Searching Authority for PCT International Patent Application No. PCT/US09/62119, dated Feb. 3, 2010, 5 pages.
(Continued)

*Primary Examiner* — Allen Porter
*Assistant Examiner* — Michael A Catina
(74) *Attorney, Agent, or Firm* — Adsero IP

(57) ABSTRACT

Tools and techniques for estimating a probability that a patient is bleeding or has sustained intravascular volume loss (e.g., due to hemodialysis or dehydration) and/or to estimate a patient's current hemodynamic reserve index, track the patient's hemodynamic reserve index over time, and/or predict a patient's hemodynamic reserve index in the future. Tools and techniques for estimating and/or predicting a patient's dehydration state. Tools and techniques for controlling a hemodialysis machine based on the patient's estimated and/or predicted hemodynamic reserve index.

42 Claims, 15 Drawing Sheets

Related U.S. Application Data

(60) Provisional application No. 61/510,792, filed on Jul. 22, 2011, provisional application No. 61/614,426, filed on Mar. 22, 2012.

(51) Int. Cl.
| | |
|---|---|
| *A61B 5/00* | (2006.01) |
| *G16H 40/60* | (2018.01) |
| *G16H 50/30* | (2018.01) |
| *A61B 5/029* | (2006.01) |
| *A61B 5/1455* | (2006.01) |
| *A61B 5/318* | (2021.01) |

(52) U.S. Cl.
CPC .......... *A61B 5/7275* (2013.01); *G16H 40/60* (2018.01); *G16H 50/30* (2018.01); *A61B 5/029* (2013.01); *A61B 5/14551* (2013.01); *A61B 5/318* (2021.01); *Y02A 90/10* (2018.01)

(56) References Cited

U.S. PATENT DOCUMENTS

| | | |
|---|---|---|
| 5,619,990 A | 4/1997 | Kanai |
| 5,853,364 A | 12/1998 | Baker, Jr. et al. |
| 5,865,168 A | 2/1999 | Isaza |
| 5,967,981 A | 10/1999 | Watrous |
| 5,984,893 A | 11/1999 | Ward |
| 6,083,172 A | 7/2000 | Baker, Jr. et al. |
| 6,094,592 A | 7/2000 | Yorkey et al. |
| 6,206,830 B1 | 3/2001 | Diab et al. |
| 6,248,080 B1 | 6/2001 | Miesel |
| 6,338,713 B1 | 1/2002 | Chamoun et al. |
| 6,371,921 B1 | 4/2002 | Caro et al. |
| 6,398,728 B1 | 6/2002 | Bardy |
| 6,409,675 B1 | 6/2002 | Turcott |
| 6,411,833 B1 | 6/2002 | Baker, Jr. et al. |
| 6,553,991 B1 | 4/2003 | Isaza |
| 6,556,852 B1 | 4/2003 | Schulze |
| 6,557,553 B1 | 5/2003 | Borrello |
| 6,558,336 B2 | 5/2003 | Collins |
| 6,589,189 B2 | 7/2003 | Meyerson et al. |
| 6,591,122 B2 | 7/2003 | Schmitt |
| 6,606,509 B2 | 8/2003 | Schmitt |
| 6,675,031 B1 | 1/2004 | Porges et al. |
| 6,721,584 B2 | 4/2004 | Baker, Jr. et al. |
| 6,739,337 B2 | 5/2004 | Isaza |
| 6,852,083 B2 | 2/2005 | Caro et al. |
| 7,160,250 B2 | 1/2007 | Lemaire |
| 7,231,245 B2 | 6/2007 | Greenwald et al. |
| 7,285,100 B2 | 10/2007 | Lemaire |
| 7,455,643 B1 | 11/2008 | Li et al. |
| 7,547,283 B2 | 6/2009 | Mourad et al. |
| 7,496,393 B2 | 11/2009 | Diab et al. |
| 7,647,185 B2 | 1/2010 | Tarassenko et al. |
| 7,654,964 B1 | 2/2010 | Kroll et al. |
| 7,668,579 B2 | 2/2010 | Lynn |
| 7,678,507 B2 | 3/2010 | Berkow et al. |
| 7,720,516 B2 | 5/2010 | Chin et al. |
| 7,865,224 B2 | 1/2011 | Baker, Jr. et al. |
| 7,873,497 B2 | 1/2011 | Weber et al. |
| 7,887,502 B2 | 2/2011 | Ross et al. |
| 7,931,559 B2 | 4/2011 | Baker, Jr. et al. |
| 7,957,780 B2 | 6/2011 | Lamego et al. |
| 7,976,472 B2 | 7/2011 | Kiani |
| 8,019,400 B2 | 9/2011 | Diab et al. |
| 8,463,346 B2 | 6/2013 | Kuhn et al. |
| 8,512,260 B2 | 8/2013 | Grudic et al. |
| 8,641,635 B2 | 2/2014 | Melker et al. |
| 9,603,534 B2 | 3/2017 | Gabbay et al. |
| 9,757,041 B2 | 9/2017 | Grudic et al. |
| 2001/0027335 A1 | 10/2001 | Meyerson et al. |
| 2003/0060690 A1 | 3/2003 | Jelliffe et al. |
| 2003/0125612 A1 | 7/2003 | Fox et al. |
| 2003/0130570 A1 | 7/2003 | Krivitski et al. |
| 2003/0176931 A1 | 9/2003 | Pednault et al. |
| 2003/0200189 A1 | 10/2003 | Meng et al. |
| 2003/0212678 A1 | 11/2003 | Bloom et al. |
| 2004/0215244 A1 | 10/2004 | Marcovecchio et al. |
| 2004/0242972 A1 | 12/2004 | Adak et al. |
| 2005/0015009 A1 | 1/2005 | Mourad et al. |
| 2005/0209516 A1 | 9/2005 | Fraden |
| 2005/0228298 A1 | 10/2005 | Banet et al. |
| 2006/0058691 A1 | 3/2006 | Kiani |
| 2006/0106743 A1 | 5/2006 | Horvitz |
| 2006/0161403 A1 | 7/2006 | Jiang et al. |
| 2006/0166176 A1 | 7/2006 | Lakin et al. |
| 2006/0178585 A1 | 8/2006 | Sharrock |
| 2006/0195041 A1 | 8/2006 | Lynn et al. |
| 2006/0253016 A1 | 11/2006 | Baker, Jr. et al. |
| 2007/0015972 A1 | 1/2007 | Wang et al. |
| 2007/0032732 A1 | 2/2007 | Shelley et al. |
| 2007/0099239 A1 | 5/2007 | Tabibiazar et al. |
| 2007/0112275 A1 | 5/2007 | Cooke et al. |
| 2007/0213619 A1 | 9/2007 | Linder |
| 2008/0039731 A1 | 2/2008 | McCombie et al. |
| 2008/0045845 A1 | 2/2008 | Pfeiffer et al. |
| 2008/0067132 A1 | 3/2008 | Ross et al. |
| 2008/0077023 A1 | 3/2008 | Campbell et al. |
| 2008/0097173 A1 | 4/2008 | Soyemi et al. |
| 2008/0133434 A1 | 6/2008 | Asar et al. |
| 2008/0146890 A1 | 6/2008 | LeBoeuf et al. |
| 2008/0146892 A1 | 6/2008 | LeBoeuf et al. |
| 2008/0154814 A1 | 6/2008 | Chaudhury et al. |
| 2008/0234607 A1 | 9/2008 | Hunter-Jones et al. |
| 2008/0294217 A1 | 11/2008 | Lian et al. |
| 2009/0005703 A1 | 1/2009 | Fasciano |
| 2009/0036754 A1 | 2/2009 | Pons et al. |
| 2009/0069647 A1 | 3/2009 | McNames et al. |
| 2009/0112106 A1 | 3/2009 | Zhang |
| 2009/0143656 A1 | 6/2009 | Manwaring et al. |
| 2009/0149724 A1 | 6/2009 | Mark et al. |
| 2009/0149751 A1 | 6/2009 | Mourad et al. |
| 2009/0204162 A1 | 8/2009 | Addison et al. |
| 2009/0264776 A1 | 10/2009 | Vardy |
| 2009/0272678 A1 | 11/2009 | Sornmo et al. |
| 2009/0281434 A1* | 11/2009 | Messerges ............... A61B 5/02 600/485 |
| 2009/0287105 A1 | 11/2009 | Hirsch |
| 2009/0292198 A1 | 11/2009 | Kleiven et al. |
| 2009/0043222 A1 | 12/2009 | Chetham |
| 2010/0016739 A1 | 1/2010 | Shelley et al. |
| 2010/0041962 A1 | 2/2010 | Causevic et al. |
| 2010/0081942 A1 | 4/2010 | Huiku |
| 2010/0094158 A1 | 4/2010 | Solem et al. |
| 2010/0160795 A1 | 6/2010 | Banet et al. |
| 2010/0191128 A1 | 7/2010 | Shelley et al. |
| 2010/0204589 A1 | 8/2010 | Swoboda et al. |
| 2010/0249559 A1 | 9/2010 | Lovejoy |
| 2011/0077532 A1 | 3/2011 | Kim et al. |
| 2011/0112799 A1 | 5/2011 | Weber et al. |
| 2011/0152651 A1 | 6/2011 | Berkow |
| 2011/0160549 A1 | 6/2011 | Saroka et al. |
| 2011/0172545 A1 | 7/2011 | Grudic et al. |
| 2011/0201962 A1 | 8/2011 | Grudic et al. |
| 2011/0282169 A1 | 8/2011 | Grudic et al. |
| 2011/0237914 A1 | 9/2011 | Lamego et al. |
| 2012/0123232 A1 | 5/2012 | Najarian et al. |
| 2012/0136224 A1 | 5/2012 | Najarian et al. |
| 2012/0184840 A1 | 7/2012 | Najarian et al. |
| 2012/0245439 A1 | 9/2012 | Andre' et al. |
| 2012/0269420 A1 | 10/2012 | Najarian et al. |
| 2012/0296219 A1 | 11/2012 | Chon et al. |
| 2012/0330117 A1 | 12/2012 | Grudic et al. |
| 2013/0041268 A1 | 2/2013 | Rimoldi et al. |
| 2013/0218056 A1 | 8/2013 | Aelen et al. |
| 2013/0245397 A1 | 9/2013 | Grudic et al. |
| 2013/0261468 A1 | 10/2013 | Semler et al. |
| 2013/0343585 A1 | 12/2013 | Bennett et al. |
| 2014/0073938 A1 | 3/2014 | Rodriguez-Llorente et al. |
| 2014/0107437 A1 | 4/2014 | Pinsky |
| 2014/0236053 A1 | 8/2014 | Walker et al. |
| 2015/0065826 A1 | 3/2015 | Mulligan et al. |
| 2015/0073723 A1 | 3/2015 | Mulligan et al. |
| 2015/0141769 A1 | 5/2015 | Mulligan et al. |

(56) References Cited

U.S. PATENT DOCUMENTS

| | | |
|---|---|---|
| 2016/0015284 A1 | 1/2016 | Grudic et al. |
| 2016/0038042 A1 | 2/2016 | Mulligan et al. |
| 2016/0038043 A1 | 2/2016 | Mulligan et al. |
| 2016/0162786 A1 | 6/2016 | Grudic et al. |
| 2016/0354039 A1 | 12/2016 | Soto et al. |
| 2016/0374625 A1 | 12/2016 | Mulligan et al. |
| 2017/0007139 A9 | 1/2017 | Grudic et al. |
| 2017/0215016 A1 | 7/2017 | Dohmen et al. |
| 2017/0258329 A1 | 9/2017 | Marsh |
| 2017/0303799 A1 | 10/2017 | Grudic et al. |
| 2017/0347177 A1 | 11/2017 | Masaki |
| 2018/0214028 A1 | 8/2018 | Zhang et al. |
| 2020/0205734 A1 | 7/2020 | Mulligan et al. |
| 2020/0205747 A1 | 7/2020 | Mulligan et al. |

FOREIGN PATENT DOCUMENTS

| | | |
|---|---|---|
| EP | 3468457 | 4/2019 |
| WO | WO 2003-077854 A2 | 9/2003 |
| WO | WO 2003-091421 A3 | 11/2003 |
| WO | WO-2005-055825 A1 | 6/2005 |
| WO | WO-2005-112756 A1 | 12/2005 |
| WO | WO 2007-011565 A1 | 1/2007 |
| WO | WO 2007-098957 A1 | 9/2007 |
| WO | WO 2007-117570 A2 | 10/2007 |
| WO | WO 2007-149533 A2 | 12/2007 |
| WO | WO 2010-009735 A2 | 1/2010 |
| WO | WO 2010-053743 A1 | 5/2010 |
| WO | WO 2010-117572 A2 | 10/2010 |
| WO | WO 2011-002904 A2 | 1/2011 |
| WO | WO 2011-050066 A2 | 4/2011 |
| WO | WO 2011-103102 A1 | 8/2011 |
| WO | WO 2011-109734 A1 | 9/2011 |
| WO | WO 2012-054880 A2 | 4/2012 |
| WO | WO 2012-166568 A3 | 12/2012 |
| WO | WO 2013-016212 A1 | 1/2013 |
| WO | WO 2014-149981 A1 | 9/2014 |
| WO | WO-2015-042484 A1 | 3/2015 |
| WO | WO 2015-069940 A1 | 5/2015 |
| WO | WO 2015-073909 A1 | 5/2015 |
| WO | WO 2015-073910 A1 | 5/2015 |
| WO | WO 2016-061542 A1 | 4/2016 |
| WO | WO 2016-061545 A1 | 4/2016 |
| WO | WO 2017-044868 A1 | 3/2017 |
| WO | WO-2017-218431 A1 | 12/2017 |

OTHER PUBLICATIONS

International Preliminary Report on Patentability prepared by the International Bureau for PCT/US2009/062119, dated May 12, 2011, 6 pages.
Decision to Grant, dated Apr. 23, 2015 for EP 09825222.4, 3 pages.
European Search Report, dated Jun. 15, 2012 for EP 09825222.4, 10 pages.
Procopio et al (2008) Intelligent Robots And Systems IEEE/RSJ International Conference, pp. 620-627, "Learning in 1-14 dynamic environments with Ensemble Selection for autonomous outdoor robot navigation".
Shoemaker, et al (2001) CHEST, 120(2):528-538, "Outcome Prediction of Emergency Patients by Noninvasive Hemodynamic Monitoring".
Supplemental European Search Report, dated Jul. 3, 2012 for EP 09825222.4, 1 page.
U.S. Appl. No. 13/126,727, filed Apr. 28, 2011 by Grudic et al. and entitled "Long Term Active Learning from Large Continually Changing Data Sets," 181 pages.
U.S. Appl. No. 13/126,727, NonFinal Office Action dated Sep. 11, 2014; 58 pages.
U.S. Appl. No. 13/126,727, Notice of Publication dated Nov. 17, 2011; 1 page.
U.S. Appl. No. 13/028,140, NonFinal Office Action dated Nov. 13, 2012; 27 pages.
U.S. Appl. No. 13/028,140, Notice of Allowance dated Feb. 22, 2013; 22 pages.
U.S. Appl. No. 13/028,140, Notice of Publication dated Aug. 18, 2011; 1 page.
U.S. Appl. No. 13/028,140, Restriction Requirement dated Aug. 1, 2012; 7 pages.
U.S. Appl. No. 13/028,140, filed Feb. 15, 2011 by Grudic et al. and entitled, "Statistical, Noninvasive Measurement of Intracranial Pressure" 41 pages.
U.S. Appl. No. 13/889,513, Notice of Publication dated Sep. 19, 2013; 1 page.
U.S. Appl. No. 13/889,513, filed May 8, 2013 by Grudic et al. and entitled "Statistical, Noninvasive Measurement of Intracranial Pressure," 35 pages.
U.S. Appl. No. 13/889,513, NonFinal Office Action dated Jun. 15, 2015, 27 pages.
International Preliminary Report on Patentability prepared by the International Bureau for PCT/US11/24938, dated Aug. 30, 2012, 7 pages.
International Search Report and Written Opinion prepared by the U.S. Patent and Trademark Office as International Searching Authority for PCT International Patent Application No. PCT/US2011/24938, dated Jun. 7, 2011, 13 pages.
Supplemental European Search Report, dated Jun. 21, 2013 for EP 11745124.5, 7 pages.
U.S. Appl. No. 13/041,006, filed Mar. 4, 2011 by Grudic et al. and entitled "Active Physical Perturbations to Enhance Intelligent Medical Monitoring" 47 pages.
U.S. Appl. No. 13/041,006, NonFinal Office Action dated May 23, 2014; 27 pages.
U.S. Appl. No. 13/041,006, NonFinal Office Action dated Dec. 22, 2014; 14 pages.
U.S. Appl. No. 13/041,006, Notice of Publication dated Jul. 14, 2011; 1 page.
International Preliminary Report on Patentability prepared by the International Bureau for PCT/US11/27237, dated Sep. 13, 2012, 10 pages.
International Search Report and Written Opinion prepared by the U.S. Patent and Trademark Office as International Searching Authority for PCT International Patent Application No. PCT/US2011/027237, dated May 27, 2011, 16 pages.
Cooke et al. (2004) Journal of Applied Physiology 96(4):1249-1261, "Lower body negative pressure as a model to study progression to acute hemorrhagic shock in humans".
Extended European Search Report, dated Oct. 18, 2013 for EP11751440.6, 7 pages.
Lambert et al. (2007) ACTA Anaesthesiologica Scandinavica 51(4):415-425, "Does a positive 1-27 end-expiratory pressure-induced reduction in stroke volume indicate preload responsiveness? An experimental study".
Ryan et al. (2008) Journal of Applied Physiology 104(5):1402-1409, "Breathing through an inspiratory threshold device improves stroke volume during central hypovolemia in humans".
Supplemental Extended European Search Report, dated Nov. 6, 2013 for EP11751440.6, 8 pages.
U.S. Appl. No. 13/554,483, filed Jul. 20, 2012 by Grudic et al. and entitled "Hemodynamic Reserve Monitor and Hemodialysis Control," 57 pages.
International Preliminary Report on Patentability prepared by the International Bureau for PCT International Patent Application No. PCT/US12/047659, dated Feb. 6, 2014, 10 pages.
International Search Report and Written Opinion prepared by the U.S. Patent and Trademark Office as International Searching Authority for PCT International Patent Application No. PCT/US12/47659, dated Oct. 12, 2012, 16 pages.
Extended European Search Report for EP 12816832.5, dated Oct. 6, 2014, 9 pages.
U.S. Appl. No. 14/535,171, Notice of Publication dated Mar. 5, 2015; 1 page.
International Search Report and Written Opinion prepared by the Korean Intellectual Property Office as International Searching Authority for PCT International Patent Application No. PCT/US2014/064413, dated Feb. 12, 2015, 13 pages.

(56) References Cited

OTHER PUBLICATIONS

International Search Report and Written Opinion prepared by the Korean Intellectual Property Office as International Searching Authority for PCT International Patent Application No. PCT/US2014/065818, dated Feb. 26, 2015, 14 pages.
International Search Report and Written Opinion prepared by the Korean Intellectual Property Office as International Searching Authority for PCT International Patent Application No. PCT/US2014/065820, dated Feb. 26, 2015, 14 pages.
Berkow (Aug. 2010) Intelomed, Inc., "CVInsight," 14 pages.
Berkow (Jan. 2012) 510(K) Summary, "CVInsight," 9 pages.
Najarian (2012) VCU School of Engineering ResearchReport, vol. 5, p. 3.
U.S. Appl. No. 13/126,727, Final Rejection dated Aug. 27, 2015; 33 pages.
U.S. Appl. No. 13/041,006, Final Rejection dated Sep. 15, 2015; 19 pages.
Canadian Patent Application No. 2,775,675, NonFinalOA dated Dec. 9, 2015; 3 pages.
International Search Report and Written Opinion prepared by the Korean Intellectual Property Office as International Searching Authority for PCT International Patent Application No. PCT/US2015/056078, dated Jan. 25, 2016, 11 pages.
International Search Report and Written Opinion prepared by the Korean Intellectual Property Office as International Searching Authority for PCT International Patent Application No. PCT/US2015/56074, dated Jan. 29, 2016, 13 pages.
Convertino, Victor, "Estimation of individual-specific progression to impending cardiovascular instability using arterial waveforms," Journal of Applied Physiology, Oct. 15, 2013, vol. 115, No. 8, pp. 1196-1202.
U.S. Appl. No. 14/542,426,Non-Final Office Action dated Feb. 26, 2016; 25 pages.
U.S. Appl. No. 13/554,483, Non-Final Office Action dated Mar. 22, 2016; 41 pages.
EP11751440.6, Office Action 94(3) dated Feb. 24, 2016, 5 pages.
U.S. Appl. No. 13/041,006, Non-final Office Action dated Apr. 22, 2016, 15 pages.
International Preliminary Report on Patentability prepared by the International Bureau for PCT International Patent Application No. PCT/US14/064413, dated May 19, 2016, 10 pages.
International Preliminary Report on Patentability prepared by the International Bureau for PCT International Patent Application No. PCT/US14/65818, dated May 26, 2016, 11 pages.
International Preliminary Report on Patentability prepared by the International Bureau for PCT International Patent Application No. PCT/US14/65820, dated May 26, 2016, 11 pages.
Stewart et al. (2016) PubMed Epub ahead of print, "The Compensatory Reserve Index Following Injury: Results of a Prospective Clinical Trial" 2 pages.
U.S. Appl. No. 14/542,426, Final Office Action dated Sep. 26, 2016, 25 pages.
Intravenous Therapy (Wikipedia) Accessed on: Sep. 27, 2016, 12 pages.
U.S. Appl. No. 13/554,483, Final Office Action dated Oct. 7, 2016, 28 pages.
International Search Report and Written Opinion prepared by the Korean Intellectual Property Office as International Searching Authority for PCT International Patent Application No. PCT/US2016/051130, dated Dec. 8, 2016, 14 pages.
U.S. Appl. No. 14/535,171, NonFinalOA dated Dec. 16, 2016, 37 pages.
U.S. Appl. No. 14/885,888, NonFinalOA dated Dec. 16, 2016, 35 pages.
Nadler et al. 2014, Shock 42(2): 93-98, "The Value of Noninvasive Measurement of the Compensatory Reserve Index in Monitoring and Triage of Patients Experiencing Minimal Blood Loss".
Nadler et al. 2017, Annals of Medicine and Surgery, "The approximated cardiovascular reserve index complies with haemorrhage related hemodynamic deterioration pattern: A swine exsanguination model" 7 pages.
Canadian Patent Application No. 2,775,675, NonFinalOA dated Nov. 9, 2016; 4 pages.
U.S. Appl. No. 13/041,006, FinalOA dated Mar. 7, 2017, 21 pages.
U.S. Appl. No. 13/554,483, Notice of Allowance dated Mar. 7, 2017, 39 pages.
U.S. Appl. No. 13/889,513, Final Rejection dated Apr. 11, 2017; 51 pages.
Schmidt et al. (1997) Stroke, "Noninvasive Prediction of Intracranial Pressure Curves Using Transcranial Doppler Ultrasonography and Blood Pressure Curves," 22 pages.
International Preliminary Report on Patentability prepared by the International Bureau for PCT/US15/56074, dated Apr. 27, 2017, 10 pages.
International Preliminary Report on Patentability prepared by the International Bureau for PCT/US15/56078, dated Apr. 27, 2017, 7 pages.
U.S. Appl. No. 14/542,426,Non-Final Office Action dated May 5, 2017; 17 pages.
U.S. Appl. No. 14/542,423, NonFinal Office Action dated May 8, 2017; 35 pages.
U.S. Appl. No. 14/885,891, NonFinal Office Action dated May 18, 2017; 29 pages.
Extended European Search Report for EP14862697.1, dated Jun. 14, 2017; 8 pages.
U.S. Appl. No. 14/885,888, FinalOA dated Jul. 27, 2017, 29 pages.
EP 11745124.5, Office Action 94(3) dated Jul. 31, 2017, 6 pages.
Kotsiantis (2007) Department of Computer Science and Technology, "Supervised Matchine Learning: A Review of Classification Techniques," 20 pages.
Wu et al, (2009) World Congress on Computer Science and Information Enginerring, "Time Series Mining Approach for Noninvasive Intracranial Pressure Assessment: an Investigation of Different Regularization Techniques," 5 pages.
Extended European Search Report, dated Jun. 7, 2017 for EP14862921.5, 8 pages.
Extended European Search Report, dated Jun. 20, 2017 for EP14859538.2, 8 pages.
International Search Report and Written Opinion prepared by the Korean Intellectual Property Office as International Searching Authority for PCT International Patent Application No. PCT/US2017/037067, dated Aug. 18, 2017, 21 pages.
U.S. Appl. No. 14/535,171, Final Office Action dated Nov. 16, 2017, 30 pages.
U.S. Appl. No. 13/889,513, NonFinal Office Action dated Dec. 1, 2017, 51 pages.
U.S. Appl. No. 14/867,938, NonFinal Office Action dated Dec. 8, 2017, 27 pages.
U.S. Appl. No. 13/041,006, NonFinal Office Action dated Dec. 15, 2017, 21 pages.
Canadian Patent Application No. 2,775,675, NonFinalOA dated Sep. 27, 2017; 4 pages.
U.S. Appl. No. 14/542,426,Non-Final Office Action dated Feb. 1, 2018, 19 pages.
U.S. Appl. No. 14/542,423, NonFinal Office Action dated Feb. 5, 2018, 24 pages.
U.S. Appl. No. 14/885,891, NonFinalOA dated Feb. 5, 2018, 22 pages.
Canadian Patent Application No. 2,871,608, NonFinalOA dated Jan. 25, 2018; 5 pages.
U.S. Appl. No. 14/885,888, NonFinal Office Action dated Mar. 15, 2018, 11 pages.
International Preliminary Report on Patentability prepared by the International Bureau for PCT/US2009/062119, dated Mar. 22, 2018, 9 pages.
U.S. Appl. No. 15/649,411, NonFinalOA dated Apr. 5, 2018, 23 pages.
Extended European Search Report for EP15850241.9, dated Apr. 5, 2018; 8 pages.

(56) References Cited

OTHER PUBLICATIONS

U.S. Appl. No. 15/007,489, NonFinal Office Action dated Jun. 13, 2018; 48 pages.
U.S. Appl. No. 14/535,1711, NonFinalOA dated Aug. 9, 2018, 23 pages.
U.S. Appl. No. 14/867,938, Notice of Allowance dated Sep. 6, 2018; 17 pages.
U.S. Appl. No. 13/889,513, Final Office Action dated Sep. 20, 2018, 25 pages.
U.S. Appl. No. 14/542,426, Final Office Action dated Sep. 27, 2018, 11 pages.
U.S. Appl. No. 14/885,888, Final Office Action dated Sep. 28, 2018, 7 pages.
U.S. Appl. No. 14/885,891, Final Office Action dated Sep. 28, 2018, 10 pages.
U.S. Appl. No. 13/041,006, Final Office Action dated Oct. 3, 2018, 9 pages.
U.S. Appl. No. 15/261,661, NonFinal Office Action dated Oct. 12, 2018, 38 pages.
Canadian Patent Application No. 2,871,608, NonFinalOA dated Nov. 22, 2018, 3 pages.
European Patent Application No. 12816832.5, NonFinalOA dated Oct. 12, 2018, 4 pages.
International Preliminary Report on Patentability prepared by the International Bureau for PCT International Patent Application No. PCT/US2017/037067, dated Dec. 27, 2018, 13 pages.
U.S. Appl. No. 14/542,423, NonFinal Office Action dated Dec. 28, 2018, 18 pages.
EPO Communication pursuant to Rules 161(2) and 162 EPC dated Feb. 1, 2019, 4 pages.
Extended European Search Report for EP16845202.7, dated Feb. 1, 2019, 6 pages.
Extended European Search Report Written Opinion for EP16845202.7, dated Mar. 11, 2019, 8 pages.
EPO Communication pursuant to Rule 70(2) and 70(a)(2) EPC, dated Mar. 13, 2019, 1 page.
U.S. Appl. No. 15/007,489, Final Office Action dated Mar. 20, 2019, 36 pages.
U.S. Appl. No. 13/041,006, NonFinalOA dated Apr. 4, 2019, 15 pages.
U.S. Appl. No. 14/542,426, NonFinalOA dated Apr. 5, 2019, 9 pages.
U.S. Appl. No. 15/261,661, FinalOA dated Apr. 5, 2019, 19 pages.
U.S. Appl. No. 13/889,513, Restriction Requirement dated Apr. 12, 2019, 9 pages.
U.S. Appl. No. 14/885,888, Final Office Action dated May 15, 2019, 21 pages.
U.S. Appl. No. 14/885,891, Final Office Action dated May 15, 2019, 18 pages.
U.S. Appl. No. 14/535,171, FinalOA dated Jul. 3, 2019, 20 pages.
U.S. Appl. No. 14/542,423, NonFinal Office Action dated Jul. 9, 2019, 17 pages.
U.S. Appl. No. 15/620,701, NonFinal Office Action dated Aug. 12, 2019, 27 pages.
Japan Patent Application No. 2017-539521 Office Action, dated Sep. 5, 2019, 7 pages.
EP Application No. 15850241.9, EP Examination Report, dated Oct. 14, 2019, 6 pages.
U.S. Appl. No. 16/726,334, filed Dec. 24, 2019 by Mulligan et al. and entitled "Device-Based Maneuver and Activity State-Based Physiologic Status Monitoring," 89 pages.
U.S. Appl. No. 16/726,337, filed Dec. 24, 2019 by Mulligan et al. and entitled "Ear-Based Physiological State Monitoring" 78 pages.
U.S. Appl. No. 14/885,888, Final Office Action dated Jan. 2, 2020, 2019, 21 pages.
U.S. Appl. No. 14/542,426, Final OA dated Dec. 20, 2019, 19 pages.
U.S. Appl. No. 15/261,661, Non-Final Rejection dated Jan. 16, 2020, 20 pages.
U.S. Appl. No. 14/535,171, Non-Final Rejection dated Jan. 23, 2020, 20 pages.
U.S. Appl. No. 13/041,006, Final Rejection dated Jan. 27, 2020; 10 pages.
U.S. Appl. No. 13/889,513, Non-Final OA, dated Jan. 28, 2020, 27 pages.
U.S. Appl. No. 14/885,891, Final Office Action dated Mar. 3, 2020, 19 pages.
U.S. Appl. No. 14/542,423, Final Office Action dated May 18, 2020, 21 pages.
U.S. Appl. No. 13/889,513, Notice of Abandonment, dated Sep. 25, 2020, 2 pages.
U.S. Appl. No. 14/535,171, Non-Final Office Action dated Oct. 5, 2020, 21 pages.
U.S. Appl. No. 14/542,423, Non-Final Office Action dated Oct. 6, 2020, 21 pages.
U.S. Appl. No. 15/620,701, Non-Final Office Action dated Oct. 21, 2020, 20 pages.
U.S. Appl. No. 13/041,006, Final Rejection, dated Jan. 7, 2021; 30 pages.
U.S. Appl. No. 14/885,888, Final Office Action dated Mar. 30, 2021, 25 pages.
U.S. Appl. No. 13/041,006, Non-Final Rejection dated Jun. 12, 2020; 29 pages.
U.S. Appl. No. 15/620,701, Final Office Action dated Jun. 22, 2020, 25 pages.
EPO Communication pursuant to Rules 71(3) dated Jun. 23, 2020, 57 pages.
U.S. Appl. No. 14/885,891, Non-Final Office Action dated Aug. 6, 2020, 19 pages.
U.S. Appl. No. 14/885,888, Non-Final Office Action dated Aug. 6, 2020, 2019, 21 pages.
U.S. Appl. No. 14/542,426, Non-Final Office Action dated Aug. 6, 2020, 2019, 19 pages.
U.S. Appl. No. 15/261,661, Non-Final Rejection dated Sep. 3, 2020, 22 pages.
U.S. Appl. No. 16/726,337, Non-Final Office Action dated May 17, 2021; 79 pages.
U.S. Appl. No. 15/261,661, Final Office Action dated May 19, 2021, 25 pages.
U.S. Appl. No. 14/535,171, Final Office Action dated May 19, 2021, 22 pages.
U.S. Appl. No. 14/542,423, Final Office Action dated May 19, 2021, 21 pages.
U.S. Appl. No. 14/542,426, Final Office Action dated Jun. 1, 2021, 20 pages.
U.S. Appl. No. 15/620,701, Non-Final Office Action dated Jun. 6, 2021, 22 pages.
U.S. Appl. No. 14/885,891, Non-Final Office Action, dated Jun. 8, 2021, 23 pages.
U.S. Appl. No. 13/041,006, Non-Final Office Action dated Jul. 16, 2021; 32 pages.
U.S. Appl. No. 16/726,337, Final Office Action dated Sep. 7, 2021, 68 pages.
U.S. Appl. No. 15/620,701, Final Office Action dated Oct. 26, 2021, 22 pages.
U.S. Appl. No. 14/885,888, Non-Final Office Action, dated Dec. 24, 2021, 28 pages.
U.S. Appl. No. 14/885,891, Final Office Action, dated Dec. 24, 2021, 24 pages.
U.S. Appl. No. 13/041,006, Final Office Action dated Jan. 27, 2022; 32 pages.
U.S. Appl. No. 14/535,171, Notice of Allowance, dated Feb. 9, 2022, 30 pages.
U.S. Appl. No. 15/261,661, Notice of Allowance, dated Mar. 10, 2022; 48 pages.
U.S. Appl. No. 14/542,423, Notice of Allowance, dated Mar. 16, 2022; 29 pages.
U.S. Appl. No. 15/620,701, Notice of Allowance, dated Mar. 30, 2022; 27 pages.
U.S. Appl. No. 14/542,426, Notice of Allowance, dated Mar. 31, 2022; 26 pages.

* cited by examiner ent disclosure may be related to the following
commonly assigned applications/patents:

This application is a continuation application of U.S. patent application Ser. No. 13/554,483 (the "'483 application"), filed Jul. 20, 2012 by Grudic et al. and entitled, "Hemodynamic Reserve Monitor and Hemodialysis Control". The '483 application claims the benefit, under 35 U.S.C. § 119(e), of provisional U.S. Patent Application No. 61/510,792, filed Jul. 22, 2011 by Grudic et al. and entitled "Cardiovascular Reserve Monitor", and provisional U.S. Patent Application No. 61/614,426, filed Mar. 22, 2012 by Grudic et al. and entitled "Hemodynamic Reserve Monitor and Hemodialysis Control", the entire teachings of which are incorporated herein by reference.

The '483 application is also a continuation-in-part of U.S. patent application Ser. No. 13/041,006 (the "'006 application"), filed Mar. 4, 2011 by Grudic et al. and entitled "Active Physical Perturbations to Enhance Intelligent Medical Monitoring," which is hereby incorporated by reference, and which claims the benefit, inter alia, of provisional U.S. Patent Application No. 61/310,583, filed Mar. 4, 2010, which is hereby incorporated by reference. The '006 application is a continuation-in-part of U.S. patent application Ser. No. 13/028,140 (the "'140 application"), filed Feb. 15, 2011 by Grudic et al. and entitled "Statistical, Noninvasive Measurement of Intracranial Pressure," which is hereby incorporated by reference, and which claims the benefit of provisional U.S. Patent Application No. 61/305,110, filed Feb. 16, 2010, by Moulton et al. and titled "A Statistical, Noninvasive Method for Measuring Intracranial Pressure," which is hereby incorporated by reference.

The '140 application is a continuation in part of International Application No. PCT/US2009/062119, filed Oct. 26, 2009 by Grudic et al. and entitled "Long Term Active Learning from Large Continually Changing Data Sets" (the "'119 application"), which is hereby incorporated by reference, and which claims the benefit, under 35 U.S.C. § 119(e), of provisional U.S. Patent Application No. 61/252,978 filed Oct. 19, 2009, U.S. Patent Application Nos. 61/166,499, 61/166,486, and 61/166,472, filed Apr. 3, 2009, and U.S. Patent Application No. 61/109,490, filed Oct. 29, 2008, each of which is hereby incorporated by reference.

The respective disclosures of these applications/patents (collectively, the "Related Applications") are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under grant number 0535269 awarded by the National Science Foundation; grant number FA8650-07-C-7702 awarded by the Air Force Research Laboratory; and grant numbers W81XWH-09-C-0160 and W81XWH-09-1-0750 awarded by Army Medical Research Material and Command. The government has certain rights in the invention.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, tools and techniques for medical monitoring, and more particularly, to tools and techniques that can monitor, estimate, and/or predict a patient's cardiac reserve.

BACKGROUND

Hemorrhagic shock induced by traumatic injury is a leading cause of mortality. The first hour following injury has been termed the "golden hour," because there is a short interval of time during which recognition and proper management of a patient with significant, ongoing bleeding can make the difference between life and death. Significant bleeding is not always clinically evident. Many severely injured patients have intracavitary bleeding, which means that bleeding from a major organ or vessel is contained within the thorax or abdomen. There is no external evidence of bleeding and as a result, suspicion and clinical signs of bleeding must be sought by the practitioner. In the field, where imaging and laboratory tests are generally not available, a change in vital signs over time may be the only indication that a patient is bleeding. Thus, during the "golden hour" one must learn to recognize the signs and symptoms of acute blood loss, then initiate fluid resuscitation and frequently estimate the patient's fluid needs in an ongoing fashion.

The problem is that humans are unable to recognize subtle, beat-to-beat vital sign changes that are indicative of bleeding. More importantly, humans are unable to detect subtle vital sign changes that lead to and are characteristic of impending hemodynamic decompensation or cardiovascular collapse, which is heralded by hypotension with bradycardia.

Thus, there is a need for tools and techniques to enable a practitioner to recognize as quickly as possible a probability that a patient is bleeding or has experienced intravascular volume loss (e.g., due to hemodialysis or dehydration) and/or to estimate a patient's current hemodynamic reserve, track the patient's hemodynamic reserve over time, and/or predict a patient's hemodynamic reserve in the future. The term "hemodynamic reserve" is a hemodynamic parameter indicative of the proportion of fluid in the vascular system between normovolemia (full reserve) and the onset of hemodynamic decompensation (no reserve). The latter is typically heralded by hypotension with bradycardia.

BRIEF SUMMARY

A set of embodiments provides tools and techniques for estimating a probability that a patient is bleeding or has experienced intravascular volume loss (e.g., due to hemodialysis, or dehydration) and/or to estimate a patient's current hemodynamic reserve, track the patient's hemodynamic reserve over time, and/or predict a patient's hemodynamic reserve in the future. Some such tools can also control the operation of therapeutic machines, such as hemodialysis machines, intravenous fluid pumps, medication delivery systems, and/or ventilators, based on the predicted hemodynamic reserve. Some embodiments can also estimate and/or predict a patient's state of dehydration.

The tools provided by various embodiments include, without limitation, methods, systems, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

For example, one set of embodiments provides methods. An exemplary method might comprise monitoring, with one or more sensors, physiological data of a patient. The method might further comprise analyzing, with a computer system, the physiological data. Many different types of physiological data can be monitored and/or analyzed by various embodiments, including without limitation, blood pressure waveform data, plethysmograph waveform data, photoplethysmograph ("PPG") waveform data (such as that generated by a pulse oximeter), and/or the like.

An apparatus, in accordance with yet another set of embodiments, might comprise a computer readable medium having encoded thereon a set of instructions executable by one or more computers to perform one or more operations. In some embodiments, the set of instructions might comprise instructions for performing some or all of the operations of methods provided by certain embodiments.

A system, in accordance with yet another set of embodiments, might comprise one or more processors and a computer readable medium in communication with the one or more processors. The computer readable medium might have encoded thereon a set of instructions executable by the computer system to perform one or more operations, such as the set of instructions described above, to name one example. In some embodiments, the system might further comprise one or more sensors and/or a therapeutic device, either or both of which might be in communication with the processor and/or might be controlled by the processor. Such sensors can include, but are not limited to, a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, an electrooculogram, a transcutaneous glucometer, an electrolyte sensor, and/or an electronic stethoscope.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Figure 1:
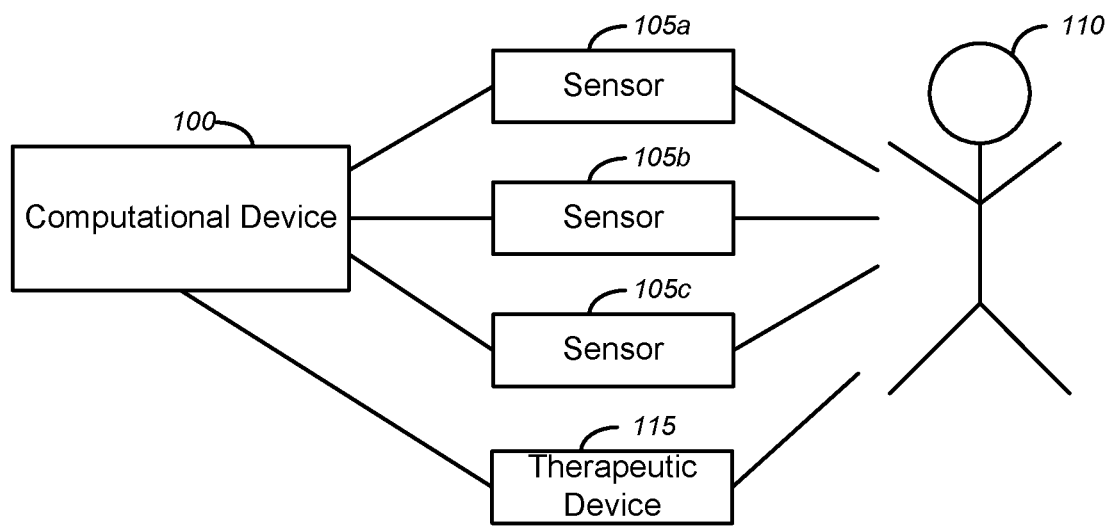
FIG. 1 is a schematic diagram illustrating a system for estimating hemodynamic reserve, in accordance with various embodiments.

The following disclosure illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Overview

A set of embodiments provides tools and techniques for estimating a probability that a patient is bleeding (e.g., internally) and/or to estimate a patient's current hemodynamic reserve, track the patient's hemodynamic reserve over time, and/or predict a patient's hemodynamic reserve in the future. Some such tools can also control the operation of therapeutic machines, such as intravenous fluid pumps, medication delivery systems, hemodialysis machines, and ventilators, based on the predicted hemodynamic reserve. Some embodiments can also estimate and/or predict a patient's state of dehydration.

A hemodynamic reserve monitor in accordance with some embodiments, (described herein as a device and/or a system), along with the methods such a monitor can perform, and the software can employ, constitutes a technology that is able to estimate the hemodynamic reserve of a patient. In an aspect, this monitor quickly, accurately and/or in real-time can determine the probability of whether a patient is bleeding. In another aspect, the device can simultaneously monitor the patient's hemodynamic reserve by tracking a hemodynamic reserve index (also referred to herein and in the Related Applications as "HDRI," and, equivalently, as a cardiovascular reserve index or "CRI"), to appropriately and effectively guide fluid resuscitation and ongoing patient care.

The Hemodynamic Reserve Index (HDRI) is a hemodynamic parameter that is indicative of the individual-specific proportion of intravascular fluid reserve remaining before the onset of hemodynamic decompensation. HDRI has values that range from 1 to 0, where values near 1 are associated with normovolemia (normal circulatory volume) and values near 0 are associated with the individual specific circulatory volume at which hemodynamic decompensation occurs.

The mathematical formula of HDRI, at some time "t" is given by the following equation:

$$HDRI(t) = 1 - \frac{BLV(T)}{BLV_{HDD}} \quad \text{(Eq. 1)}$$

Where BLV(t) is the intravascular volume loss ("BLV," also referred to as "blood loss volume" in the related applications) of a person at time "t," and $BLV_{HDD}$ is the intravascular volume loss of a person when they enter hemodynamic decompensation ("HDD"). Hemodynamic decompensation is generally defined as occurring when the systolic blood pressure falls below 70 mmHg. This level of intravascular volume loss is individual specific and will vary from subject to subject.

Lower body negative pressure (LBNP) in some linear or nonlinear relationship λ with intravascular volume loss:

$$BLV = \lambda \cdot LBNP \quad \text{(Eq. 2)}$$

can be used in order to estimate the HDRI for an individual undergoing a LBNP experiment as follows:

$$HDRI = 1 - \frac{BLV(t)}{BLV_{HDD}} \approx 1 - \frac{\lambda \cdot LBNP(t)}{\lambda \cdot LBNP_{HDD}} = 1 - \frac{LBNP(t)}{LBNP_{HDD}} \quad \text{(Eq. 3)}$$

Where LBNP(t) is the LBNP level that the individual is experiencing at time "t", and, $LBNP_{HDD}$ is the LNPB level that the individual will enter hemodynamic decompensation.

A measure of HDRI is useful in a variety of clinical settings, including but not limited to: 1) acute blood loss volume due to injury or surgery; 2) acute circulatory volume loss due to hemodialysis (also called intradialytic hypotension); and 3) acute circulatory volume loss due to various causes of dehydration (e.g. reduced fluid intake, vomiting, dehydration, etc.). A change in HDRI can also herald other conditions, including without limitation general fatigue, overheating and certain types of illnesses. Accordingly, the tools and techniques for estimating and/or predicting HDRI can have a variety of applications in a clinical setting, including without limitation diagnosing such conditions.

In various embodiments, a hemodynamic reserve monitor can include, but is not limited to, some or all of the following functionality, as described in further detail herein:

A. Estimating and/or displaying intravascular volume loss to hemodynamic decompensation (or cardiovascular collapse).

B. Estimating, predicting and/or displaying a patient's hemodynamic reserve as an index that is proportional to an approximate measure of intravascular volume loss to CV collapse, recognizing that each patient has a unique reserve capacity.

C. Estimating, predicting and/or displaying a patient's hemodynamic reserve as an index with a normative value at euvolemia (for example, HDRI=1), representing a state in which the patient is normovolemic; a minimum value (for example, HDRI=0) which implies no circulatory reserve and that the patient is experiencing CV collapse; and/or an excess value (for example, HDRI>1) representing a state in which the patient is hypervolemic; the patient's normalized hemodynamic reserve can be displayed on a continuum between the minimum and maximum values (perhaps labeled by different symbols and/or colors depending on where the patient falls on the continuum).

D. Determining and/or displaying a probability that bleeding or intravascular volume loss has occurred.

E. Displaying an indicator that intravascular volume loss has occurred and/or is ongoing; as well as other measures of reserve, such as trend lines.

In various embodiments, HDRI estimates can be (i) based on a fixed time history of patient monitoring (for example a 30 second or 30 heart beat window); (ii) based on a dynamic time history of patient monitoring (for example monitoring for 200 minutes may use all sensor information gathered during that time to refine and improve HDRI estimates); (iii) based on either establishing a baseline estimate of HDRI when the patient is normovolemic (no volume loss has occurred); and/or (iv) based on NO baselines estimates when patient is normovolemic.

Certain embodiments can also recommend treatment options, based on the analysis of the patient's condition (including the probability of bleeding, state of dehydration, and/or the patient's estimated and/or predicted HDRI). Treatment options can include, without limitation, such things as optimizing hemodynamics, ventilator adjustments, IV fluid adjustments, transfusion of blood or blood products, infusion of volume expanders, medication changes, changes in patient position and surgical therapy.

As a specific example, certain embodiments can be used as an input for a hemodialysis procedure. For example, certain embodiments can predict how much intravascular (blood) volume can be safely removed from a patient during a hemodialysis process. For example, an embodiment might provide instructions to a human operator of a hemodialysis machine, based on estimates or predictions of the patient's HDRI. Additionally and/or alternatively, such embodiments can be used to continuously self-adjust the ultra-filtration rate of the hemodialysis equipment, thereby completely avoiding intradialytic hypotension and its associated morbidity.

As another example, certain embodiments can be used to estimate and/or predict a dehydration state (and/or the amount of dehydration) in an individual (e.g., a trauma patient, an athlete, an elder living at home, etc.) and/or to provide treatment (either by providing recommendations to treating personnel or by directly controlling appropriate therapeutic equipment). For instance, if an analytical model indicates a relationship between HDRI (and/or any other physiological phenomena that can be measured and/or estimated using the techniques described herein and in the Related Applications) and dehydration state, an embodiment can apply that model, using the techniques described herein, to estimate a dehydration state of the patient.

Exemplary Systems and Methods

FIG. 1 provides a general overview of a system provided by certain embodiments. The system includes a computer system 100 in communication with one or more sensors 105, which are configured to obtain physiological data from the subject (e.g., animal or human test subject or patient) 110. In one embodiment, the computer system 100 comprises a Lenovo THINKPAD X200, 4 GB of RAM with Microsoft WINDOWS 7 operating system and is is programmed with software to execute the computational methods outlined herein. The computational methods can be implemented in MATLAB 2009b and C++ programming languages. A more general example of a computer system 100 that can be used in some embodiments is described in further detail below. Even more generally, however, the computer system 100 can be any system of one or more computers that are capable of performing the techniques described herein. In a particular embodiment, for example, the computer system 100 is capable of reading values from the physiological sensors 105, generating models of physiological state from those sensors, and/or employing such models to make individual-specific estimations, predictions, or other diagnoses, displaying the results, recommending and/or implementing a therapeutic treatment as a result of the analysis, and/or archiving (learning) these results for use in future, model building and predictions.

The sensors 105 can be any of a variety of sensors (including without limitation those described herein) for obtaining physiological data from the subject. An exemplary sensor suite might include a Finometer sensor for obtaining a noninvasive continuous blood pressure waveform, a pulse oximeter sensor, an Analog to Digital Board (National Instruments USB-9215A 16-Bit, 4 channel) for connecting the sensors (either the pulse oximeter and/or the finometer) to the computer system 100. More generally, in an embodiment one or more sensors 105 might obtain, e.g., using one or more of the techniques described herein, continuous physiological waveform data, such as continuous blood pressure. Input from the sensors 105 can constitute continuous data signals and/or outcomes that can be used to generate, and/or can be applied to, a predictive model as described below.

In some cases, the structure might include a therapeutic device 115 (also referred to herein as a "physiological assistive device"), which can be controlled by the computer system 100 to administer therapeutic treatment, in accordance with the recommendations developed by analysis of a patient's physiological data. In a particular embodiment, the therapeutic device might comprise hemodialysis equipment (also referred to as a hemodialysis machine), which can be controlled by the computer system 100 based on the estimated HDRI of the patient, as described in further detail below. Further examples of therapeutic devices in other embodiments can include a cardiac assist device, a ventilator, an automatic implantable cardioverter defibrillator ("AICD"), pacemakers, an extracorporeal membrane oxygenation circuit, a positive airway pressure ("PAP") device (including without limitation a continuous positive airway pressure ("cPAP") device or the like), an anesthesia machine, an integrated critical care system, a medical robot, intravenous and/or intra-arterial pumps that can provide fluids and/or therapeutic compounds (e.g., through intravenous injection), a heating/cooling blanket, and/or the like.

Figure 2:
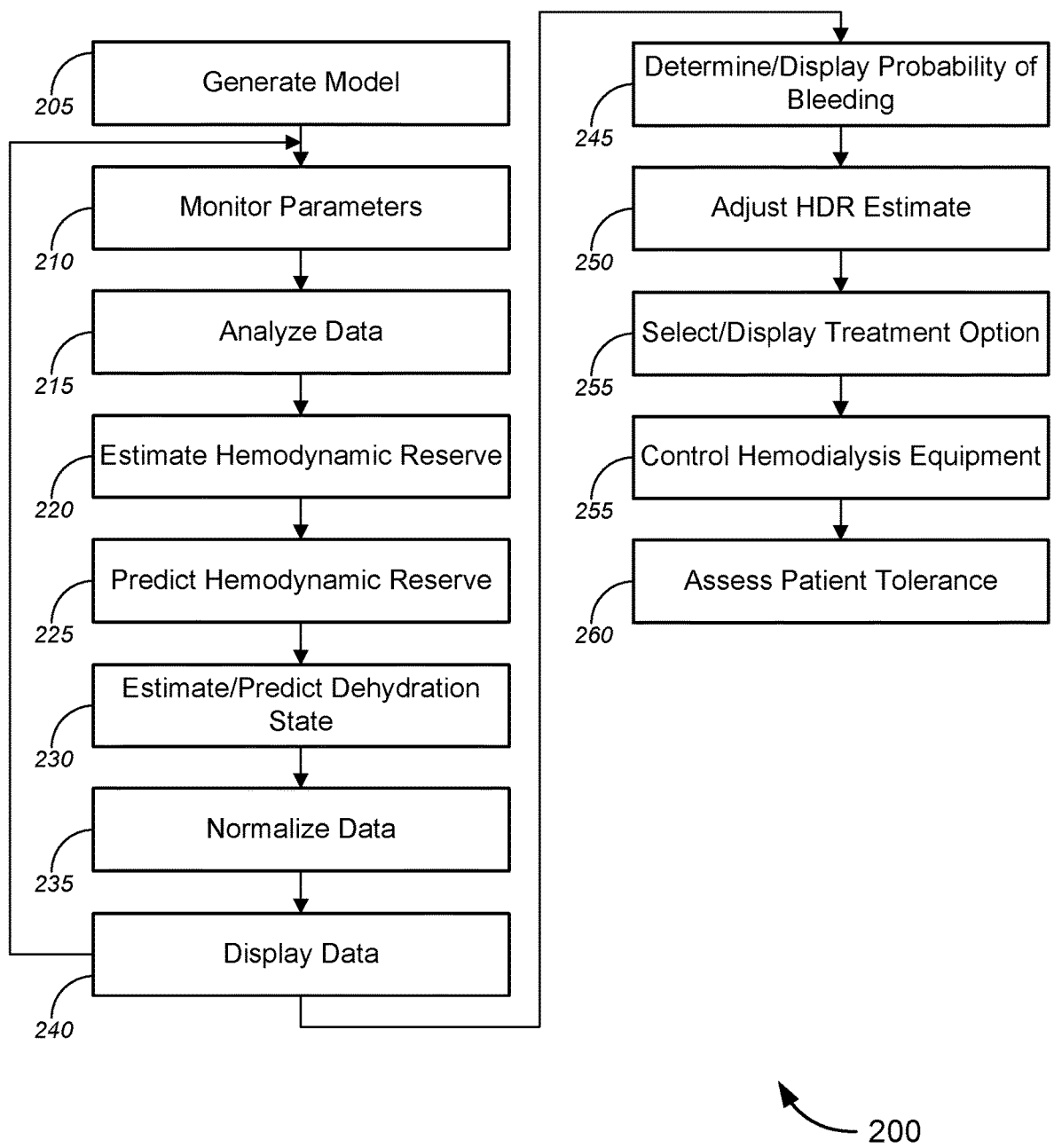
FIG. 2 is a process flow diagram illustrating a method estimating a patient's hemodynamic reserve and/or dehydration state, in accordance with various embodiments.
Figure 3:
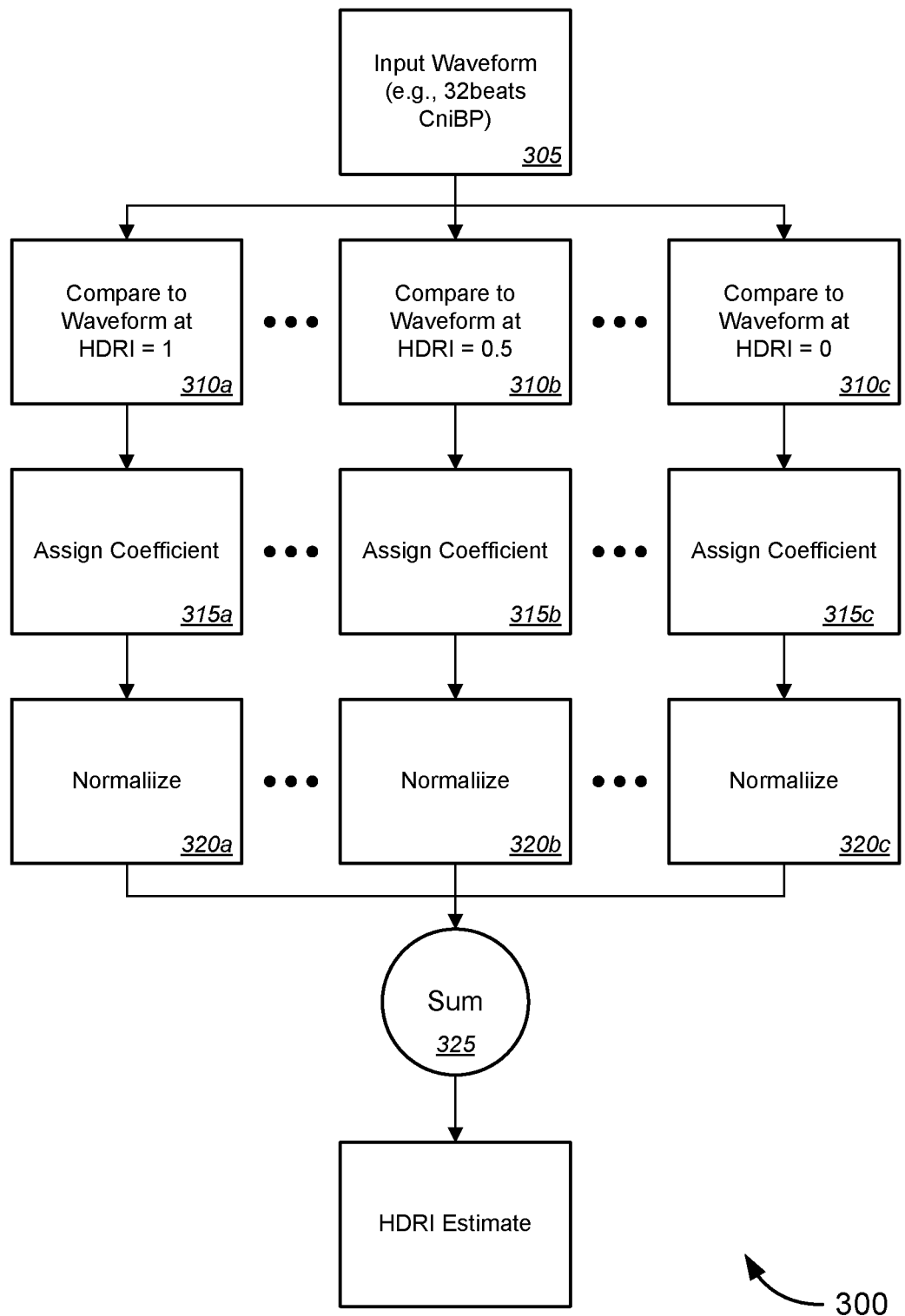
FIG. 3 illustrates a technique for estimating and/or predicting a patient's hemodynamic reserve index, in accordance with various embodiments.
Figure 11:
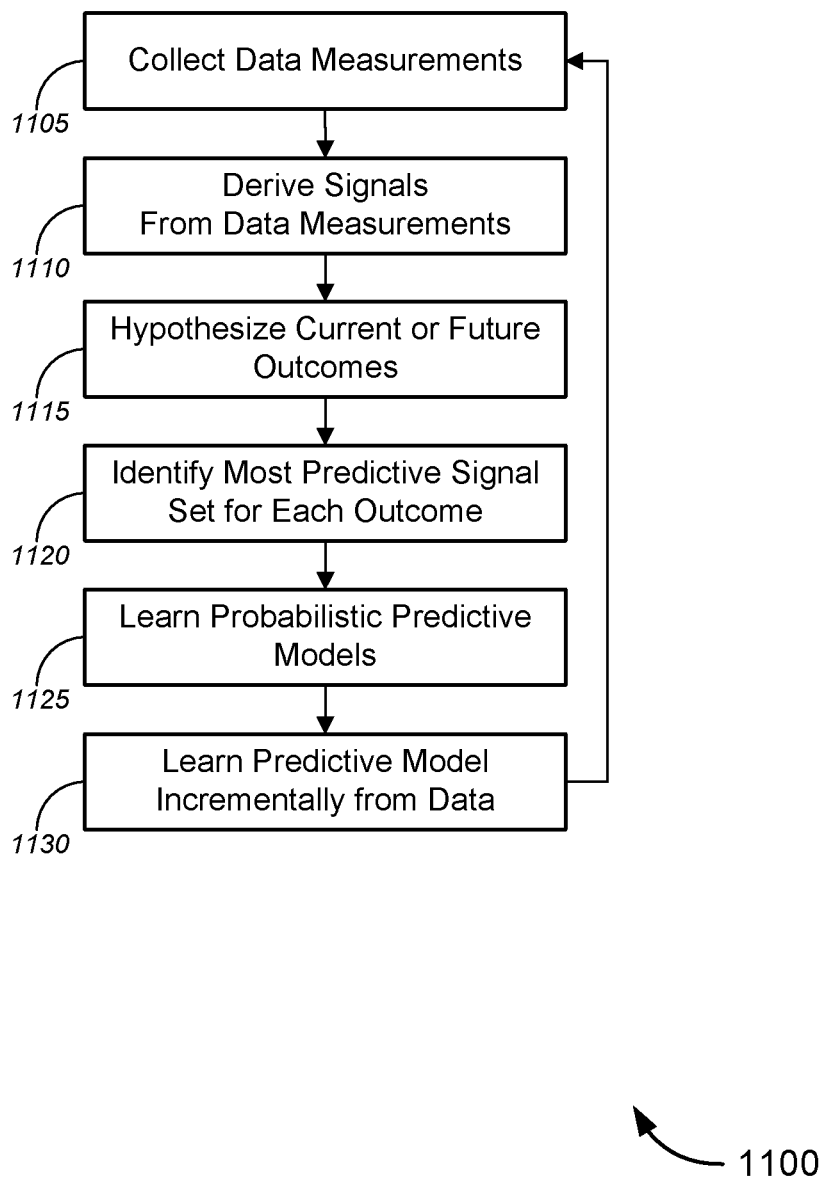
FIG. 11 is a process flow diagram illustrating a method of generating a model of a physiological state, in accordance with various embodiments.

FIGS. 2, 3 and 11 illustrate methods and screen displays in accordance with various embodiments. While the methods of FIGS. 2, 3 and 11 are illustrated, for ease of description, as different methods, it should be appreciated that the various techniques and procedures of these methods can be combined in any suitable fashion, and that, in some embodiments, the methods depicted by FIGS. 2, 3 and 11 can be considered interoperable and/or as portions of a single method. Similarly, while the techniques and procedures are depicted and/or described in a certain order for purposes of illustration, it should be appreciated that certain procedures may be reordered and/or omitted within the scope of various embodiments. Moreover, while the methods illustrated by FIGS. 2, 3 and 11 can be implemented by (and, in some cases, are described below with respect to) the computer system 100 of FIG. 1 (or components thereof), these methods may also be implemented using any suitable hardware implementation. Similarly, while the computer system 100 of FIG. 1 (and/or components thereof) can operate according to the methods illustrated by FIGS. 2, 3 and 11 (e.g., by executing instructions embodied on a computer readable medium), the system 100 can also operate according to other modes of operation and/or perform other suitable procedures.

Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

By way of non-limiting example, various embodiments can comprise a method for using sensor data to predict and/or estimate a patient's hemodynamic reserve (in real-time, after every heartbeat, or as the information is needed) and/or dehydration state. FIG. 2 illustrates an exemplary method 200 in accordance with various embodiments. The method 200 might comprise generating a model, e.g., with a computer system, against which patient data can be analyzed to estimate and/or predict various physiological states (block 205). Such a model can be generated using a number of different techniques.

In a general sense, generating the model can comprise receiving data pertaining to a plurality of more physiological parameters of a test subject to obtain a plurality of physiological data sets; directly measuring one or more physiological states of the test subject with a reference sensor to obtain a plurality of physiological state measurements; and correlating the received data with the physiological state measurements of the test subject. The one or more physiological states can include, without limitation, a state of hypervolemia, a state of euvolemia, and/or a state of cardiovascular collapse (or near-cardiovascular collapse). In fact, there are a variety of techniques for generating a model in accordance with different embodiments. One exemplary technique for generating a model of a generic physiological state is described below with respect to FIG. 11, below. Any suitable technique or model may be employed in accordance with various embodiments, however.

A number of physiological states can be modeled, and a number of different conditions can be imposed on test subjects as part of the model generation. For example, in some cases, one or more test subjects might be subjected to LBNP. In an exemplary case, LBNP data is collected from human subjects being exposed to progressively lower levels of LBNP, until hemodynamic decompensation, at which time LBNP is released and the subject recovers. Each level of LBNP represents an additional amount of blood loss. During these tests, physiological data (including without limitation waveform data, such as continuous non-invasive blood pressure data)) can be collected before, during, and/or after the application of the LBNP. As noted above, a relationship (as expressed by Equation 2) can be identified between LBNP and intravascular volume loss, and this relationship can be used to estimate HDRI. Hence, LBNP studies form a framework (methodology) for the development of the hemodynamic parameter referred to herein as HDRI and can be used to generate models of this parameter.

More generally, several different techniques that induce a physiological state of reduced volume in the circulatory system, e.g., to a point of cardiovascular collapse (hemodynamic decompensation) or to a point near cardiovascular collapse, can be used to generate such a model. LBNP can be used to induce this condition, as noted above. In some cases, such as in a study described below, dehydration can be used to induce this condition as well. Other techniques are possible as well. Similarly, data collected from a subject in a state of euvolemia, dehydration, hypervolemia, and/or other states might be used to generate an HDRI model in different embodiments.

Another example of a model that can be generated by various embodiments is a probability of bleeding model. In such a case, data can be collected from a number of test subjects before, during, and after bleeding (which can be measured directly in the test procedure). This data can then be used (e.g., using the techniques described below with respect to FIG. 11) to derive a model that can be used to assess the probability that a patient is bleeding.

At block 210, the method 200 comprises monitoring, with one or more sensors, physiological data of a patient. As noted above, a variety of physical parameters can be monitored, invasively and/or non-invasively, depending on the nature of the anticipated physiological state of the patient. For example, if cardiovascular collapse is a concern, the patient's blood pressure and/or other parameters might be monitored. In an aspect, monitoring the one or more physical parameters might comprise receiving, e.g., from a physiological sensor, continuous waveform data, which can be sampled as necessary. Such data can include, without limitation, blood pressure waveform data, plethysmograph waveform data, photoplethysmograph ("PPG") waveform data (such as that generated by a pulse oximeter), and/or the like The method 200 might further comprise analyzing, with a computer system, the physiological data (block 215). In some cases, the physiological data is analyzed against a pre-existing model (which, in turn, can be updated based on the analysis, as described in further detail below and in the Related Applications). Based on this analysis, the method 200, in an exemplary embodiment, includes estimating, with the computer system, a hemodynamic reserve of the patient, based on analysis of the physiological data (block 220). In some cases, the method might further comprise predicting, with the computer system, the hemodynamic reserve of the patient at one or more time points in the future, based on analysis of the physiological data (block 225). The operations to predict a future value of a parameter can be similar to those for estimating a current value; in the prediction context, however, the applied model might correlate measured data in a test subject with subsequent values of the diagnostic parameter, rather than contemporaneous values. It is worth noting, of course, that in some embodiments, the same model can be used to both estimate a current value and predict future values of a physiological parameter.

The estimated and/or predicted hemodynamic reserve of the patient can be based on several factors. Merely by way of example, in some cases, the estimated/predicted hemodynamic reserve can be based on a fixed time history of monitoring the physiological data of the patient and/or a dynamic time history of monitoring the physiological data of the patient. In other cases, the estimated/predicted hemodynamic reserve can be based on a baseline estimate of the patient's hemodynamic reserve established when the patient is euvolemic. In still other cases, the estimate and/or prediction might not be based on a baseline estimate of the patient's hemodynamic reserve established when the patient is euvolemic.

Merely by way of example, FIG. 3 illustrates one technique 300 for deriving an estimate of HDRI in accordance with some embodiments. The illustrated technique comprises sampling waveform data (e.g., any of the data described herein and in the Related Applications, including without limitation arterial waveform data, such as continuous noninvasive blood pressure waveforms) for a specified period, such as 32 heartbeats (block 305). That sample is compared with a plurality of waveforms of reference data corresponding to different HDRI values (block 310). (These reference waveforms might be derived using the algorithms described in the Related Applications, might be the result of experimental data, and/or the like). Merely by way of example, the sample might be compared with waveforms corresponding to an HDRI of 1 (block 310a), an HDRI of 0.5 (block 310b), and an HDRI of 0 (block 310c), as illustrated. From the comparison, a similarity coefficient is calculated (e.g., using a least squares or similar analysis) to express the similarity between the sampled waveform and each of the reference waveforms (block 315). These similarity coefficients can be normalized (if appropriate) (block 320), and the normalized coefficients can be summed (block 325) to produce an estimated value of the patient's HDRI.

Returning to FIG. 2, the method 200 can comprise estimating and/or predicting a patient's dehydration state (block 230). The patient's state of dehydration can be expressed in a number of ways. For instance, the state of dehydration might be expressed as a normalized value (for example, with 1.0 corresponding to a fully hydrated state and 0.0 corresponding to a state of morbid dehydration). In other cases, the state of dehydration might be expressed as a missing volume of fluid or as a volume of fluid present in the patient's system, or using any other appropriate metric.

A number of techniques can be used to model dehydration state. Merely by way of example, as noted above (and described in further detail below), the relationship between a patient's hemodynamic reserve and level of dehydration can be modeled. Accordingly, in some embodiments, estimating a dehydration state of the patient might comprise estimating the hemodynamic reserve (e.g., HDRI) of the patient, and then, based on that estimate and the known relationship, estimating the dehydration state. Similarly, a predicted value of hemodynamic reserve at some point in the future can be used to derive a predicted dehydration state at that point in the future. Other techniques might use a parameter other than HDRI to model dehydration state.

The method 200 might further comprise normalizing the results of the analysis (block 235), such as the hemodynamic reserve, dehydration state, and/or probability of bleeding, to name a few examples. Merely by way of example, the estimated/predicted hemodynamic reserve of the patient can be normalized relative to a normative normal blood volume value corresponding to euvolemia, a normative excess blood volume value corresponding to circulatory overload, and a normative minimum blood volume value corresponding to cardiovascular collapse. Any values can be selected as the normative values. Merely by way of example, in some embodiments, the normative excess blood volume value is >1, the normative normal blood volume value is 1, and the normative minimum blood volume value is 0. As an alternative, in other embodiments, the normative excess blood volume value might be defined as 1, the normative normal blood volume value might be defined as 0, and the normative minimum blood volume value at the point of cardiovascular collapse might be defined as −1. As can be seen from these examples, different embodiments might use a number of different scales to normalize HDRI and other estimated parameters.

In an aspect, normalizing the data can provide benefits in a clinical setting, because it can allow the clinician to quickly make a qualitative judgment of the patient's condition, while interpretation of the raw estimates/predictions might require additional analysis. Merely by way of example, with regard to the estimate of the hemodynamic reserve of the patient, that estimate might be normalized relative to a normative normal blood volume value corresponding to euvolemia and a normative minimum blood volume value corresponding to cardiovascular collapse. Once again, any values can be selected as the normative values. For example, if the normative normal blood volume is defined as 1, and the normative minimum blood volume value is defined as 0, the normalized value, falling between 0.0 and 1.0 can quickly apprise a clinician of the patient's location on a continuum between euvolemia and cardiovascular collapse. Similar normalizing procedures can be implemented for other estimated data (such as probability of bleeding, dehydration, and/or the like).

The method 200 might further comprise displaying data with a display device (block 240). Such data might include an estimate and/or prediction of the hemodynamic reserve of the patient and/or an estimate and/or prediction of the patient's dehydration state. A variety of techniques can be used to display such data. Merely by way of example, in some cases, displaying the estimate of the hemodynamic reserve of the patient might comprise displaying the normalized estimate of the hemodynamic reserve of the patient. Alternatively and/or additionally, displaying the normalized estimate of the hemodynamic reserve of the patient might comprise displaying a graphical plot showing the normalized excess blood volume value, the normalized normal blood volume value, the normalized minimum blood volume value, and the normalized estimate of the hemodynamic reserve (e.g., relative to the normalized excess blood volume value, the normalized normal blood volume value, the normalized minimum blood volume value).

To illustrate, FIGS. 4-10 illustrate exemplary screen captures from a display device of a hemodynamic reserve monitor, showing various features that can be provided by one or more embodiments.

Figure 4:
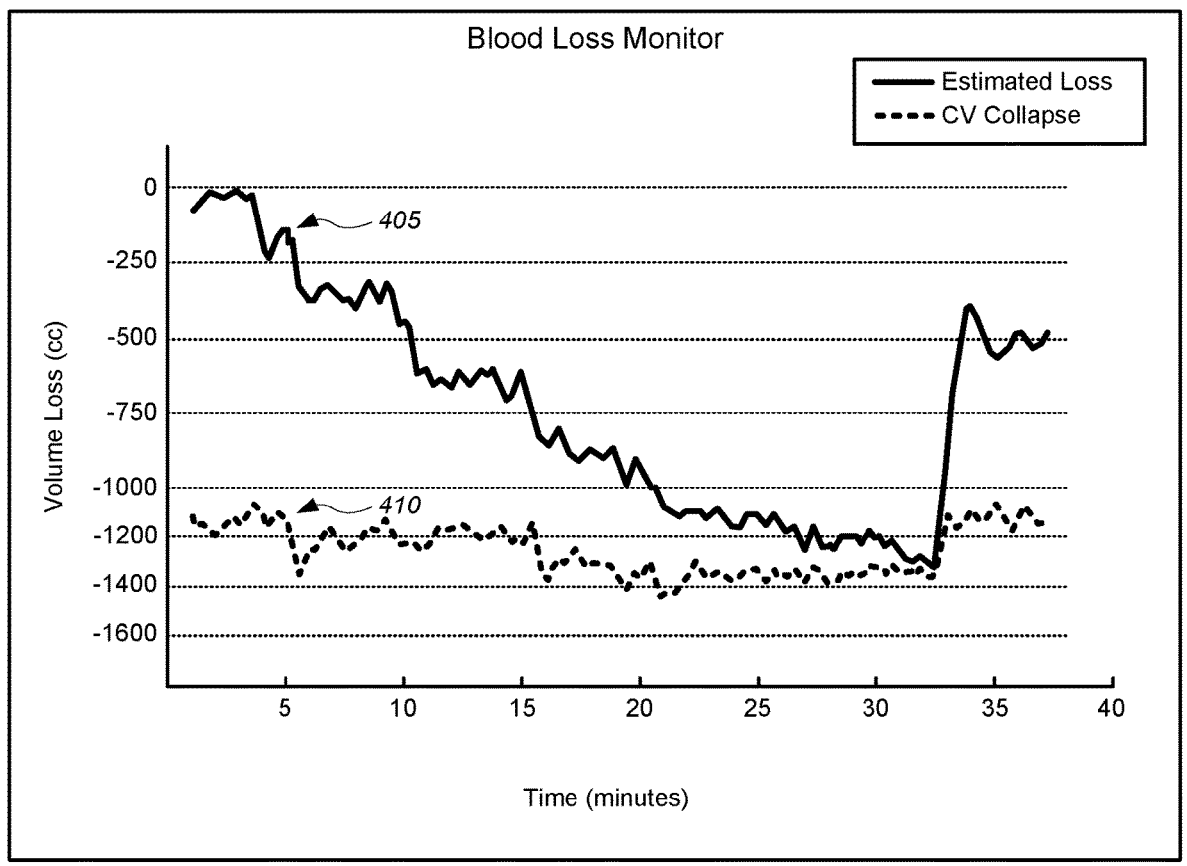
FIGS. 4-10 are exemplary screen captures illustrating display features of a hemodynamic reserve monitor, in accordance with various techniques.

FIG. 4 illustrates a display 400 from a prototype device that is designed to give medical personnel the ability to quickly assess how much blood a patient has lost (solid lines 405, which might correspond to red lines on a color display). More importantly, the monitor provides real-time information on the rate of bleeding and the patient's predicted level for CV collapse (dashed lines 410, which might correspond to blue lines on a color display). If the red 405 and blue 410 waveforms continue to converge, bleeding is ongoing. If the red waveform 405 flattens, IV fluid therapy is keeping up with blood loss. If the red 405 and blue 410 waveforms are diverging, then the provider knows, in real-time, that IV fluid resuscitation efforts are effective. Hemodynamic reserve is here measured as the distance between the red 405 and blue line 410, with CV collapse occurring when the two lines meet.

Figure 5:
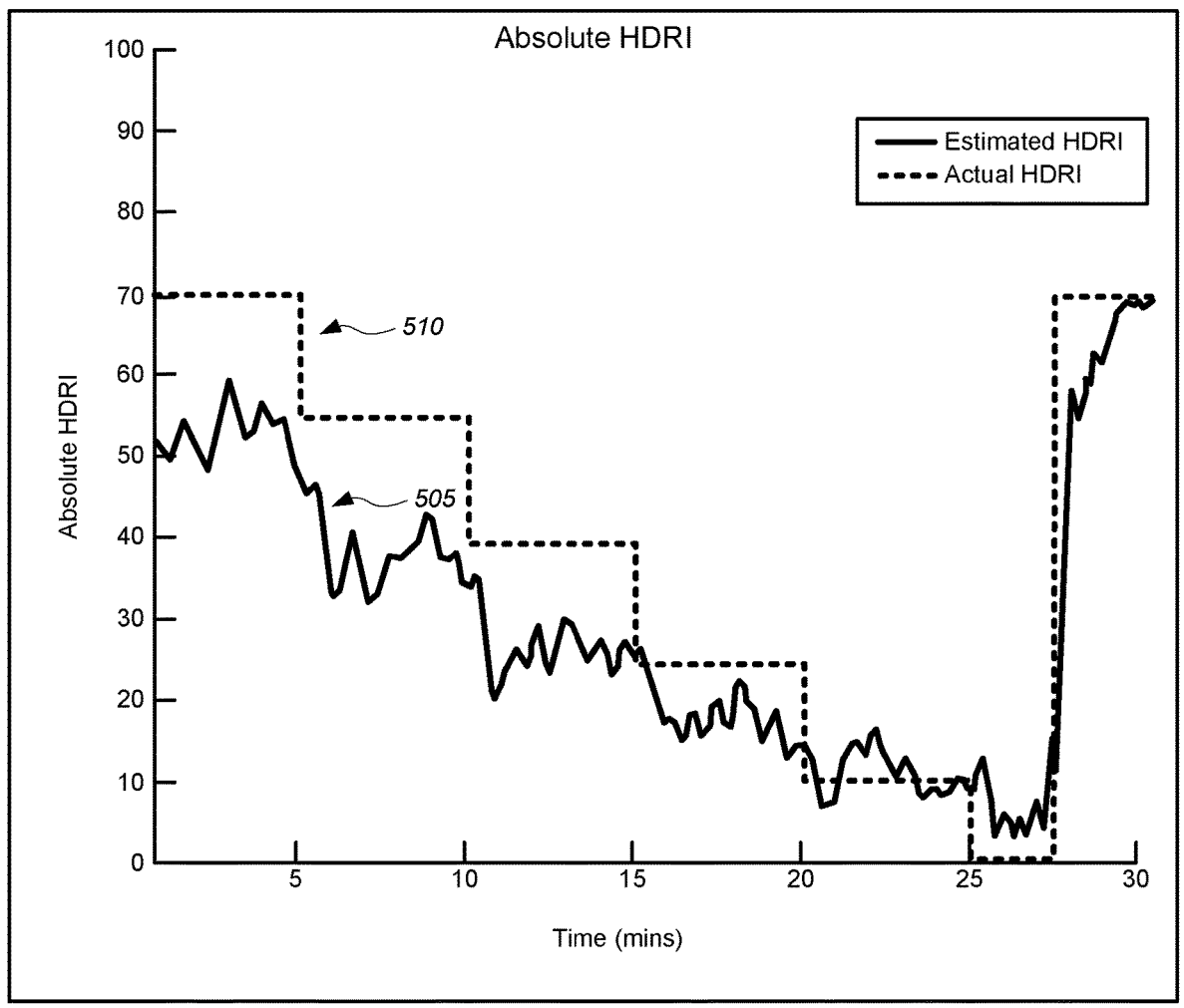

FIG. 5 shows an implementation of an "Absolute Hemodynamic Reserve Index (HDRI)" monitor screen display 500 and results on data gathered from a subject at the USAISR in the LBNP studies described herein (and in further detail in the Related Applications). The solid line 505 (which might be light green in a color display) shows the estimated Absolute HDRI and the dashed line 510 (which might be red in a color display) the actual, measured HDRI. The Y-axis is an absolute measure of HDRI, with each patient starting with a different amount of fluid reserve.

Figure 6:
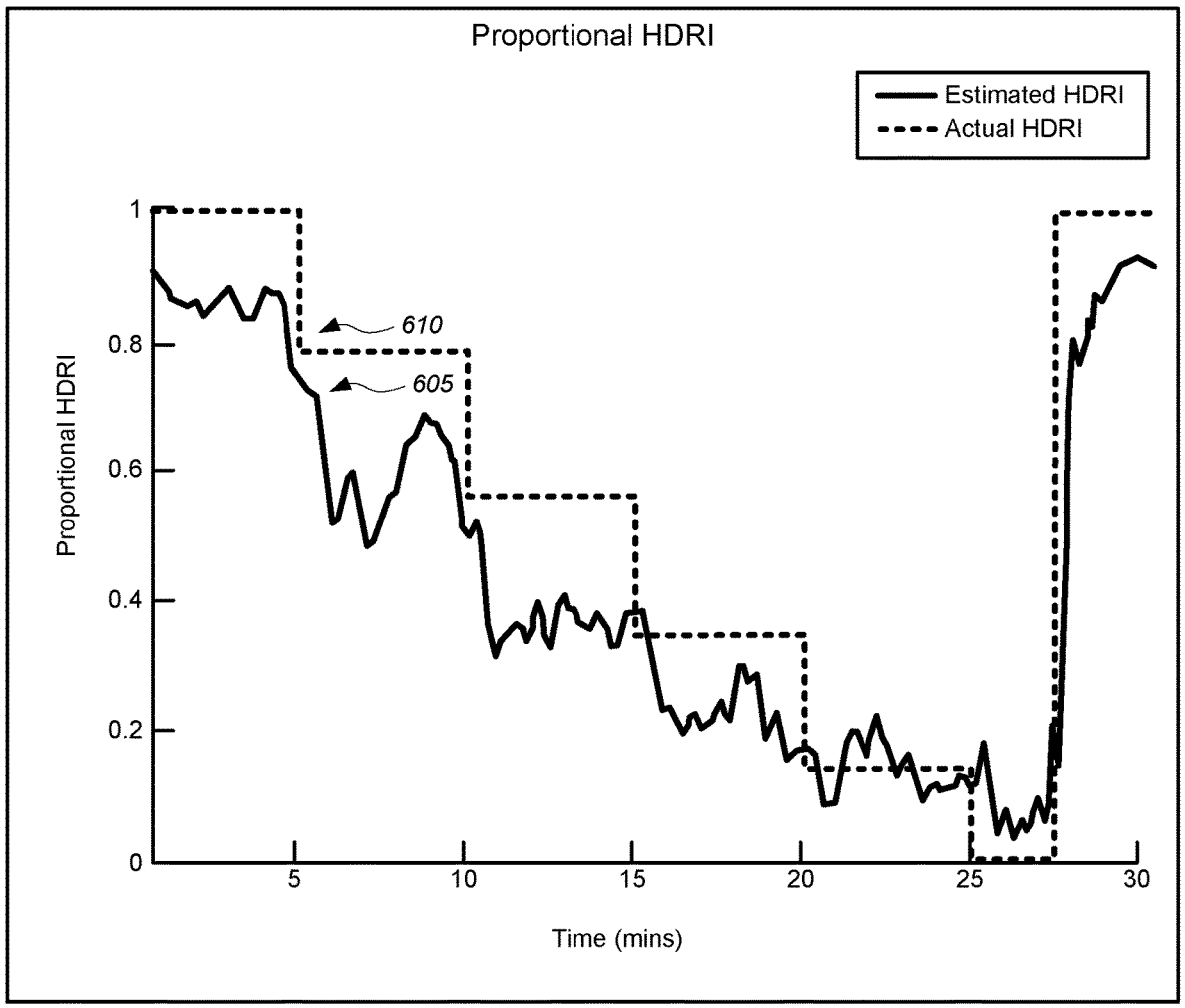

In contrast, FIG. 6 shows an implementation of a "Proportional Hemodynamic reserve Index (HDRI)" monitor and results on the data gathered from the same subject. The solid line 605 (which might be light green in a color display) shows the estimated Normalized HDRI and the dashed line 610 (which might be red in a color display) the actual, measured HDRI. The Y-axis is a proportional measure of HDRI, with a value of 1 indicating that the patient has full volume of fluid and is not bleeding, and 0 indicating that the patient is in CV collapse. HDRI values in between 0 and 1 show a continuum of fluid reserve as the patient loses fluid volume.

Figure 10:
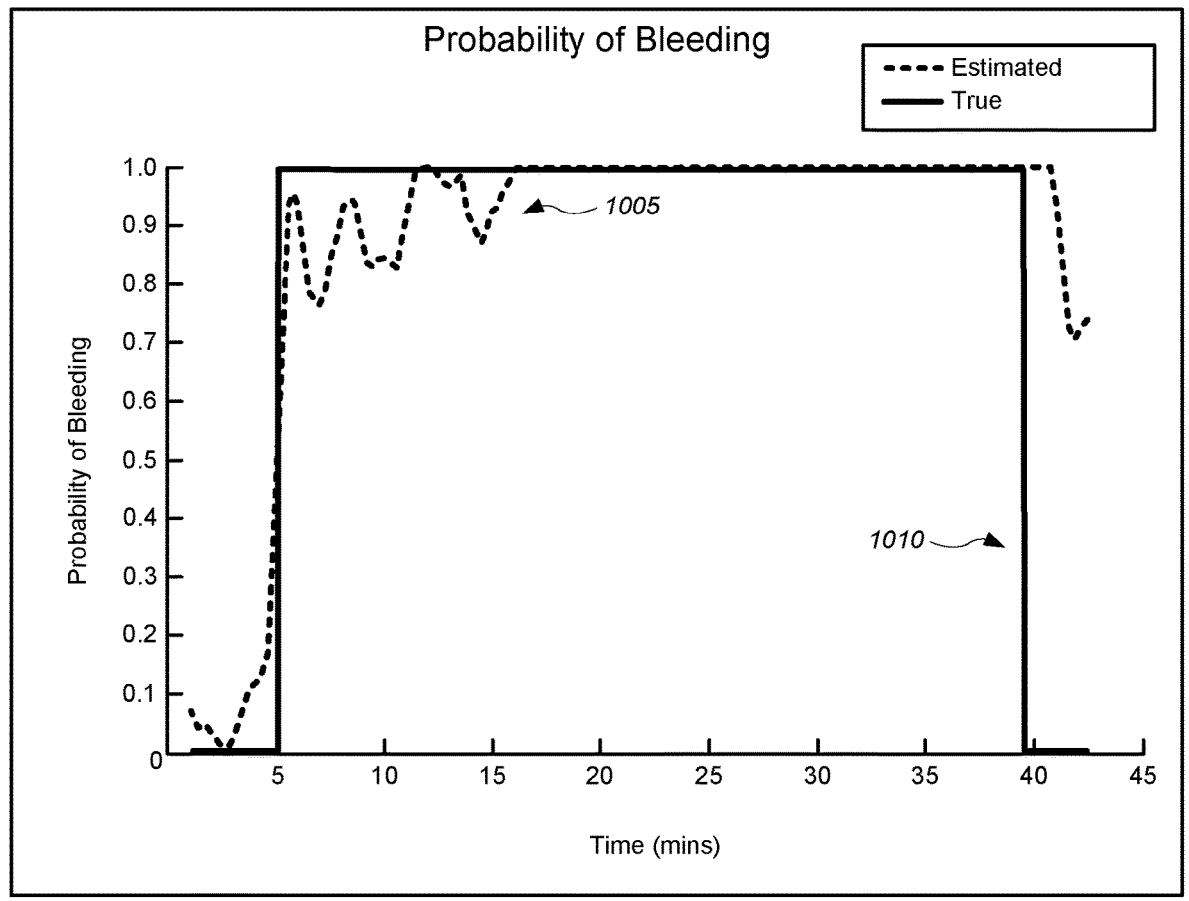

It should be noted that the "actual" HDRI values illustrated on FIGS. 5 and 6, as well as the "actual" probability of bleeding on FIG. 10, correspond to LBNP levels applied to the text subject during the trials described above and in the Related Applications. This actual HDRI can be calculated after an LBNP experiment is completed using Eq. 2, above. Moreover, in a typical clinical setting, the screen displays of FIGS. 5, 6, and 10 typically would not include a tracing for an "actual" value, since the actual value is unknown—as noted above, it may not be feasible to measure these parameters directly, so many embodiments would only include the tracings of the estimated values. The tracings of actual values are included herein to illustrate the degree of correspondence between the estimates provided by various embodiments and the actual values of the estimated parameters.

Figure 7:
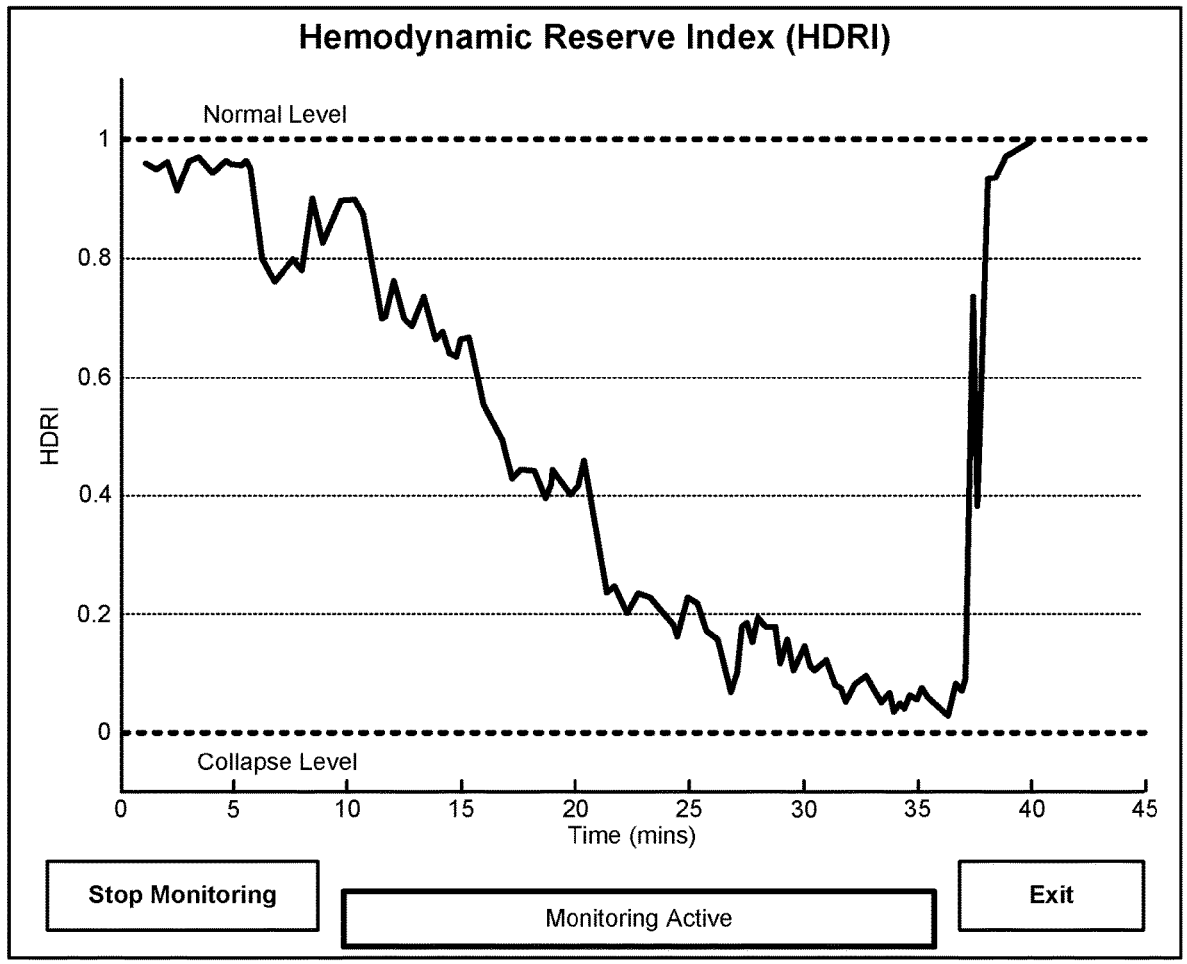

FIG. 7 illustrates an exemplary display 700 of a HDRI monitor implementation where a normalized HDRI of "1" implies circulatory volume is normal, and "0" implies no circulatory reserve and the patient is experiencing CV collapse. Values in between "0" and "1" imply a continuum of reserve.

Figure 8A:
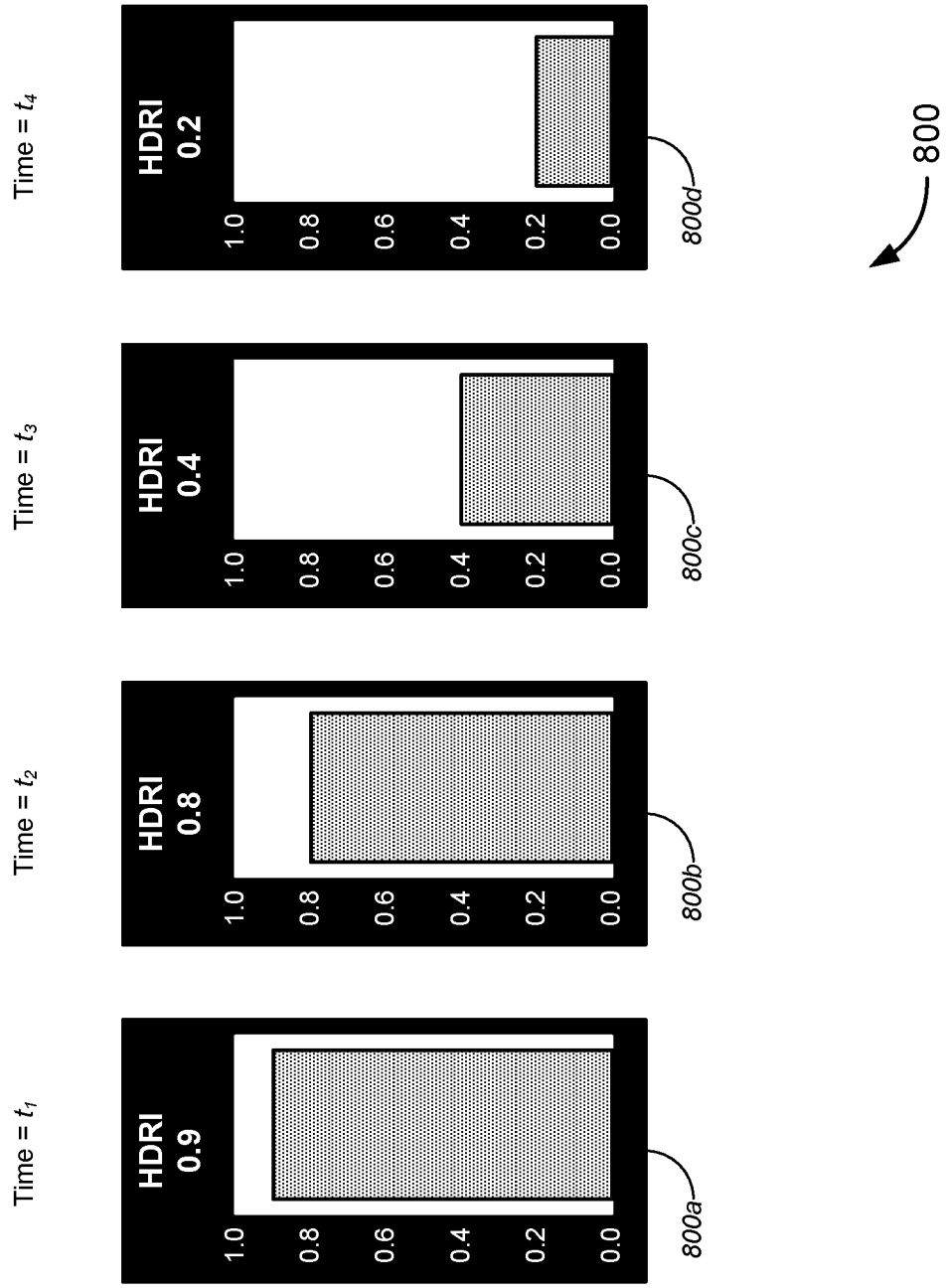

FIG. 8A illustrates four screen captures 800 of a display of a HDRI monitor implementation that displays HDRI as a "fuel gauge" type bar graph for a person undergoing central volume blood loss during an LBNP study. While FIG. 7 illustrates a trace of HDRI over time, the bar graphs of FIG. 7 provide snapshots of HDRI at the time of each screen capture. (In the illustrated implementation, the bar graphs are continuously and/or periodically updates, such that each bar graph could correspond to a particular position on the X-axis of FIG. 7.)

Figure 8B:
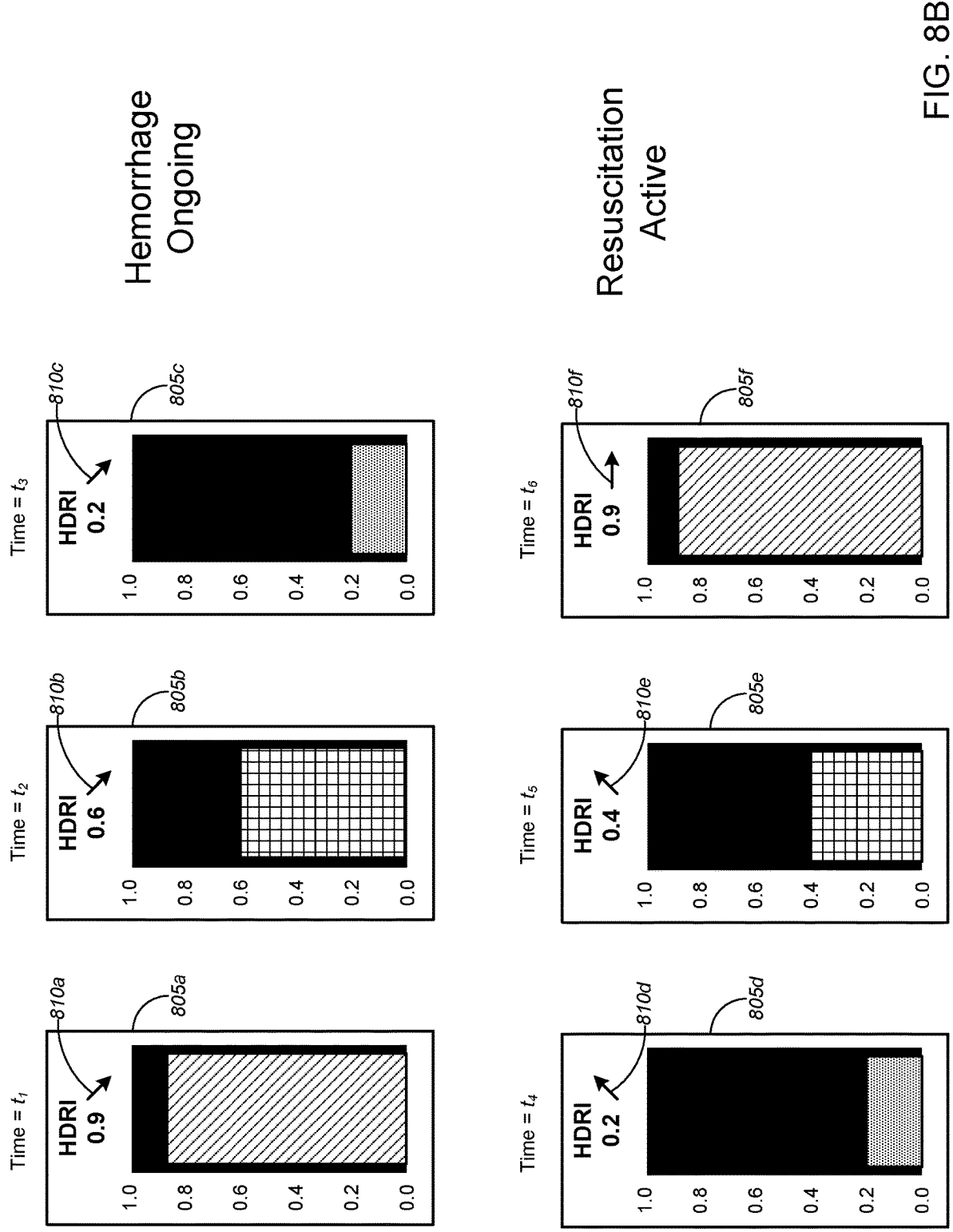

A variety of additional features are possible. Merely by way of example FIG. 8B illustrates similar "fuel gauge" type displays, but the displays 805 of FIG. 8B feature bars of different colors—for example, green (illustrated by diagonal cross-hatching), yellow (illustrated by a checked pattern) and red illustrated by gray shading) corresponding to different levels of HDRI, along with arrows 910 indicating trending in the HDRI values (e.g., rising, declining, or remaining stable).

Figure 9:
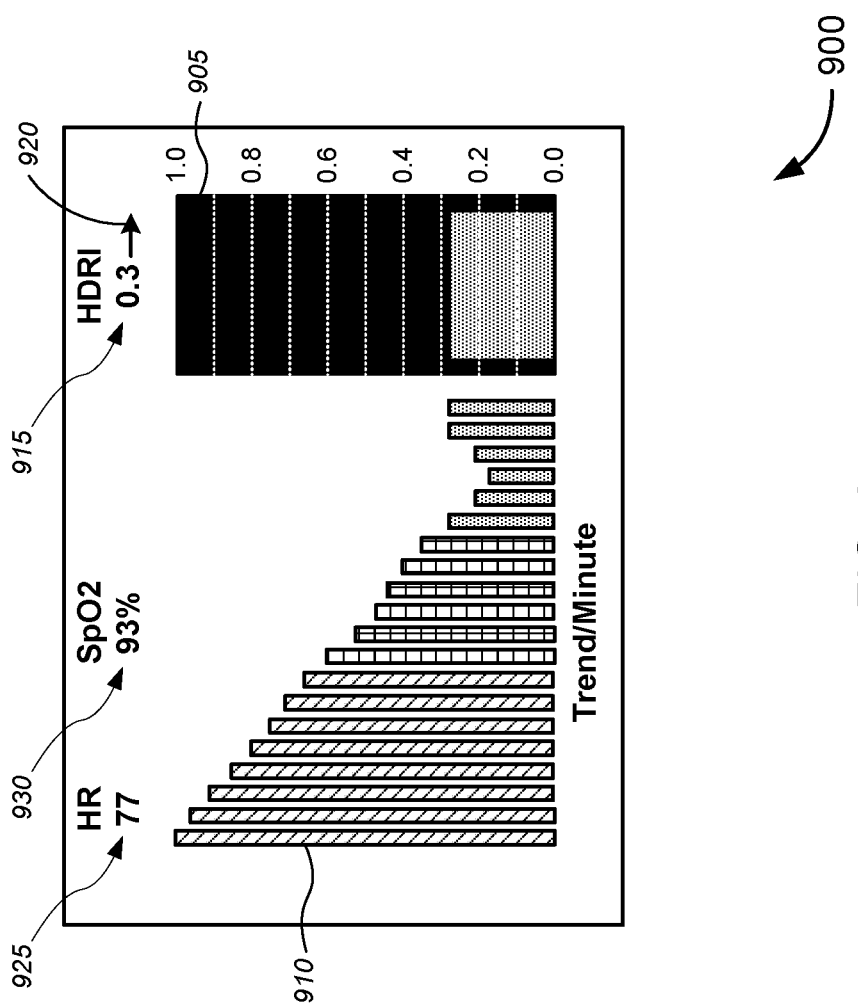

In some embodiments, such a "fuel gauge" display (or other indicator of HDRI and/or different physiological parameters) can be incorporated in a more comprehensive user interface. Merely by way of example, FIG. 9 illustrates an exemplary display 900 of a monitoring system. The display 900 includes a graphical, color-coded "fuel gauge" type display 905 of the current estimated HDRI (similar to the displays illustrated by FIG. 8B), along with a historical display 910 of recent HDRI estimates; in this example, each bar on the historical display 910 might correspond to an estimate performed every minute, but different estimate frequencies are possible, and in some embodiments, the operator can be given the option to specify a different frequency. In the illustrated embodiment, the display 900 also includes numerical display 915 of the current HDRI as well as a trend indicator 920 (similar to that indicated above). In particular embodiments, the display 900 can include additional information (and, in some cases, the types of information displayed and/or the type of display can be configured by the operator). For instance, the exemplary display 900 includes an indicator 925 of the patient's current heart rate and an indicator 930 of the patient's blood oxygen saturation level (SpO2). Other monitored parameters might be displayed as well, such as an ECG tracing, probability of bleeding estimates, and/or the like.

Returning to FIG. 2, in some cases, the method 200 might comprise repeating the operations of monitoring physiological data of the patient, analyzing the physiological data, and estimating (and/or predicting) the hemodynamic reserve of the patient, to produce a new estimated (and/or predicted) hemodynamic reserve of the patient. Thus, displaying the estimate (and/or prediction) of the hemodynamic reserve of the patient might comprises updating a display of the estimate of the hemodynamic reserve to show the new estimate (and/or prediction) of the hemodynamic reserve, in order to display a plot of the estimated hemodynamic reserve over time. Hence, the patient's hemodynamic reserve can be repeatedly estimated and/or predicted on any desired interval (e.g., after every heartbeat), on demand, etc.

In further embodiments, the method 200 can comprise determining a probability that the patient is bleeding, and/or displaying, with the display device, an indication of the probability that the patient is bleeding (block 245). For example, some embodiments might generate a model based on data that removes fluid from the circulatory system (such as LBNP, dehydration, etc.). Another embodiment might generate a model based on fluid removed from a subject voluntarily, e.g., during a blood donation, based on the known volume (e.g., 500 cc) of the donation. Based on this model, using techniques similar to those described above, a patient's physiological data can be monitored and analyzed to estimate a probability that the patient is bleeding (e.g., internally).

FIG. 10, for instance, depicts an exemplary screen display 1000 of an HDRI monitor displaying an estimate, over time, of the probability that a patient is bleeding. A probability close to "1" indicates that bleeding is or has occurred, while a probability near "0" indicates that bleeding is unlikely. In this example, the dashed line shows the estimated probability that the patient is bleeding, while the solid line shows an actual probability (which may be omitted in a clinical setting, since the actual probability (which is binary) may be difficult to ascertain clinically.

In some cases, the probability that the patient is bleeding can be used to adjust the patient's estimated HDRI. Specifically, give a probability of bleeding expressed as Pr_Bleed at a time t, the adjusted value of HDRI can be expressed as:

$$\text{HDRI}_{Adjusted}(t) = 1 - ((1 - \text{HDRI}(t)) \times Pr\_\text{Bleed}(t)) \quad \text{(Eq. 4)}$$

Given this relationship, the estimated HDRI can be adjusted to produce a more accurate diagnosis of the patient's condition at a given point in time.

The method 200 might comprise selecting, with the computer system, a recommended treatment option for the patient, and/or displaying, with the display device, the recommended treatment option (block 255). The recommended treatment option can be any of a number of treatment options, including without limitation, optimizing hemodynamics of the patient, a ventilator adjustment, an intravenous fluid adjustment, transfusion of blood or blood products to the patient, infusion of volume expanders to the patient, a change in medication administered to the patient, a change in patient position, and surgical therapy.

In a specific example, the method might comprise controlling operation of hemodialysis equipment (block 260), based at least in part on the estimate of the patient's hemodynamic reserve. Merely by way of example, a computer system that performs the monitoring and estimating functions might also be configured to adjust an ultra-filtration rate of the hemodialysis equipment in response to the estimated HDRI values of the patient. In other embodiments, the computer system might provide instructions or suggestions to a human operator of the hemodialysis equipment, such as instructions to manually adjust an ultra-filtration rate, etc.

In some embodiments, the method 200 might include assessing the tolerance of an individual to blood loss, general volume loss, and/or dehydration (block 265). For example, such embodiments might include estimating a patient's HDRI based on the change in a patient's position (e.g., from lying prone to standing, lying prone to sitting, and/or sitting to standing). Based on changes to the patient's HDRI in response to these maneuvers, the patient's sensitivity to blood loss, volume loss, and/or dehydration can be measured. In an aspect, this measurement can be performed using an HDRI model generated as described above; the patient can be monitored using one or more of the sensors described above, and the changes in the sensor output when the subject changes position can be analyzed according to the model (as described above, for example) to assess the tolerance of the individual to volume loss. Such monitoring and/or analysis can be performed in real time.

FIG. 11 illustrates a method of employing such a self-learning predictive model (or machine learning) method 1100, according to some embodiments. In particular, the method 1100 can be used to correlate physiological data received from a subject sensor with a measured physiological state. More specifically, with regard to various embodiments, the method 1100 can be used to generate a model for predicting and/or estimating various physiological parameters, such as HDRI, the probability that a patient is bleeding, a patient's dehydration state, and/or the like.

The method 1100 begins at block 1105 by collecting raw data measurements that may be used to derive a set of D data signals $s_1, \ldots, s_D$ as indicated at block 1110 (each of the data signals s being, in a particular case, input from one or many different physiological sensors). Embodiments are not constrained by the type of measurements that are made at block 1105 and may generally operate on any data set. For example, data signals can be retrieved from a computer memory and/or can be provided from a sensor or other input device. As a specific example, the data signals might correspond to the output of the sensors described above (which measure the types of waveform data described above, such as continuous, non-invasive blood pressure waveform data).

A set of K current or future outcomes $\vec{o}=(o_1, \ldots, o_K)$ is hypothesized at block 1115 (the outcomes o being, in this case, past and/or future physiological states, such as HDRI, dehydration state, probability of bleeding, etc.). The method autonomously generates a predictive model M that relates the derived data signals $\vec{s}$ with the outcomes $\vec{o}$. As used herein, "autonomous," means "without human intervention."

As indicated at block 1120, this is achieved by identifying the most predictive set of signals $S_k$, where $S_k$ contains at least some (and perhaps all) of the derived signals $s_1, \ldots, s_D$ for each outcome $o_k$, where $k \in \{1, \ldots, K\}$. A probabilistic predictive model $\hat{o}_k = M_k(S_k)$ is learned at block 1125, where $\hat{o}_k$ is the prediction of outcome $o_k$ derived from the model $M_k$ that uses as inputs values obtained from the set of signals $S_k$, for all $k \in \{1, \ldots, K\}$. The method 1100 can learn the predictive models $\hat{o}_k = M_k(S_k)$ incrementally (block 1130) from data that contains example values of signals $s_1, \ldots, s_D$ and the corresponding outcomes $o_1, \ldots, o_K$. As the data become available, the method 1100 loops so that the data are added incrementally to the model for the same or different sets of signals $S_k$, for all $k \in \{1, \ldots, K\}$.

While the description above outlines the general characteristics of the methods, additional features are noted. A linear model framework may be used to identify predictive variables for each new increment of data. In a specific embodiment, given a finite set of data of signals and outcomes $\{(\vec{s}_1, \vec{o}_1), (\vec{s}_2, \vec{o}_2), \ldots\}$, a linear model may be constructed that has the form, for all $k \in \{1, \ldots, K\}$, $$\hat{o}_k = f_k(a_0 + \Sigma_{i=1}^d a_i s_i) \quad \text{(Eq. 5)}$$

where $f_k$ is any mapping from one input to one output, and $a_0, a_1, \ldots, a_d$ are the linear model coefficients. The framework used to derive the linear model coefficients may estimate which signals $s, s_1, \ldots, s_d$ are not predictive and accordingly sets the corresponding coefficients $a_0, a_1, \ldots, a_d$ to zero. Using only the predictive variables, the model builds a predictive density model of the data, $\{(\vec{s}_1, \vec{o}_1), (\vec{s}_2, \vec{o}_2), \ldots\}$. For each new increment of data, a new predictive density models can be constructed.

In some embodiments, a prediction system can be implemented that can predict future results from previously analyzed data using a predictive model and/or modify the predictive model when data does not fit the predictive model. In some embodiments, the prediction system can make predictions and/or to adapt the predictive model in real-time. Moreover, in some embodiments, a prediction system can use large data sets not only to create the predictive model, but also predict future results as well as adapt the predictive model.

In some embodiments, a self-learning, prediction device can include a data input, a processor and an output. Memory can include application software that when executed can direct the processor to make a prediction from input data based on a predictive model. Any type of predictive model can be used that operates on any type of data. In some embodiments, the predictive model can be implemented for a specific type of data. In some embodiments, when data is received the predictive model can determine whether it understands the data according to the predictive model. If the data is understood, a prediction is made and the appropriate output provided based on the predictive model. If the data is not understood when received, then the data can be added to the predictive model to modify the model. In some embodiments, the device can wait to determine the result of the specified data and can then modify the predictive model accordingly. In some embodiments, if the data is understood by the predictive model and the output generated using the predictive model is not accurate, then the data and the outcome can be used to modify the predictive model. In some embodiments, modification of the predictive model can occur in real-time.

Particular embodiments can employ the tools and techniques described in the Related Applications in accordance with the methodology described herein perform the functions of a cardiac reserve monitor, as described herein. These functions include, but are not limited to monitoring, estimating and/or predicting a subject's (including without limitation, a patient's) hemodynamic reserve, estimating and/or determining the probability that a patient is bleeding (e.g., internally) and/or has been bleeding, recommending treatment options for such conditions, and/or the like. Such tools and techniques include, in particular, the systems (e.g., computer systems, sensors, therapeutic devices, etc.) described in the Related Applications, the methods (e.g., the analytical methods for generating and/or employing analytical models, the diagnostic methods, etc.), and the software programs described herein and in the Related Applications, which are incorporated herein by reference.

Figure 12:
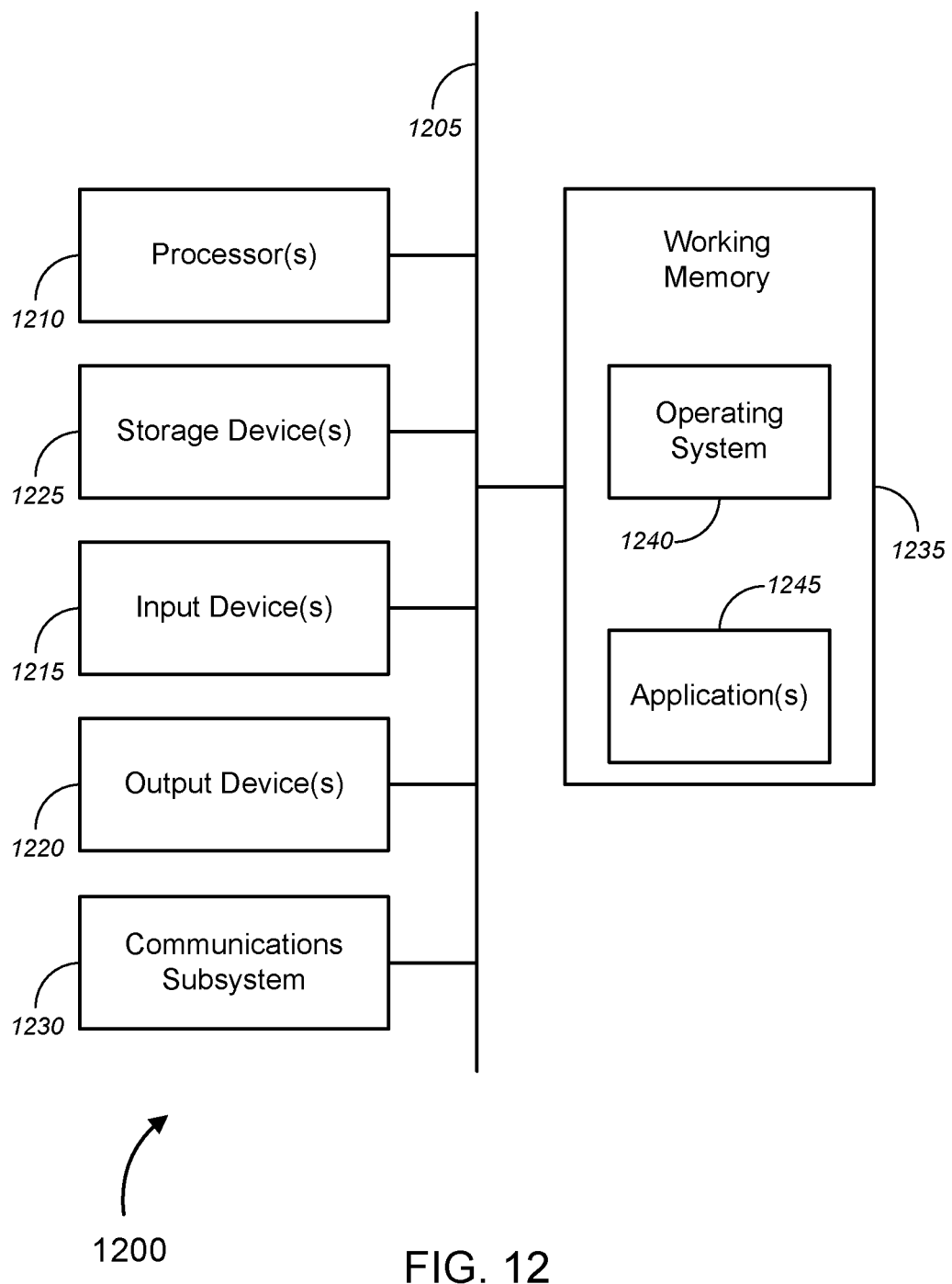
FIG. 12 is a generalized schematic diagram illustrating a computer system, in accordance with various embodiments.

Hence, FIG. 12 provides a schematic illustration of one embodiment of a computer system 1200 that can perform the methods provided by various other embodiments, as described herein, and/or can function as an HDRI monitor, etc. It should be noted that FIG. 12 is meant only to provide a generalized illustration of various components, of which one or more (or none) of each may be utilized as appropriate. FIG. 12, therefore, broadly illustrates how individual system elements may be implemented in a relatively separated or relatively more integrated manner.

The computer system 1200 is shown comprising hardware elements that can be electrically coupled via a bus 1205 (or may otherwise be in communication, as appropriate). The hardware elements may include one or more processors 1210, including without limitation one or more general-purpose processors and/or one or more special-purpose processors (such as digital signal processing chips, graphics acceleration processors, and/or the like); one or more input devices 1215, which can include without limitation a mouse, a keyboard and/or the like; and one or more output devices 1220, which can include without limitation a display device, a printer and/or the like.

The computer system 1200 may further include (and/or be in communication with) one or more storage devices 1225, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 1200 might also include a communications subsystem 1230, which can include without limitation a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1230 may permit data to be exchanged with a network (such as the network described below, to name one example), with other computer systems, and/or with any other devices described herein. In many embodiments, the computer system 1200 will further comprise a working memory 1235, which can include a RAM or ROM device, as described above.

The computer system 1200 also may comprise software elements, shown as being currently located within the working memory 1235, including an operating system 1240, device drivers, executable libraries, and/or other code, such as one or more application programs 1245, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1225 described above. In some cases, the storage medium might be incorporated within a computer system, such as the system 1200. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer system 1200 and/or might take the form of source and/or installable code, which, upon compilation and/or installation on the computer system 1200 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 1200) to perform methods in accordance with various embodiments of the invention. According to a set of embodiments, some or all of the procedures of such methods are performed by the computer system 1200 in response to processor 1210 executing one or more sequences of one or more instructions (which might be incorporated into the operating system 1240 and/or other code, such as an application program 1245) contained in the working memory 1235. Such instructions may be read into the working memory 1235 from another computer readable medium, such as one or more of the storage device(s) 1225. Merely by way of example, execution of the sequences of instructions contained in the working memory 1235 might cause the processor(s) 1210 to perform one or more procedures of the methods described herein.

The terms "machine readable medium" and "computer readable medium," as used herein, refer to any medium that participates in providing data that causes a machine to operation in a specific fashion. In an embodiment implemented using the computer system 1200, various computer readable media might be involved in providing instructions/code to processor(s) 1210 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 1225. Volatile media includes, without limitation, dynamic memory, such as the working memory 1235. Transmission media includes, without limitation, coaxial cables, copper wire and fiber optics, including the wires that comprise the bus 1205, as well as the various components of the communication subsystem 1230 (and/or the media by which the communications subsystem 1230 provides communication with other devices). Hence, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1210 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 1200. These signals, which might be in the form of electromagnetic signals, acoustic signals, optical signals and/or the like, are all examples of carrier waves on which instructions can be encoded, in accordance with various embodiments of the invention.

The communications subsystem 1230 (and/or components thereof) generally will receive the signals, and the bus 1205 then might carry the signals (and/or the data, instructions, etc. carried by the signals) to the working memory 1235, from which the processor(s) 1205 retrieves and executes the instructions. The instructions received by the working memory 1235 may optionally be stored on a storage device 1225 either before or after execution by the processor(s) 1210.

Clinical Examples

Figure 13:
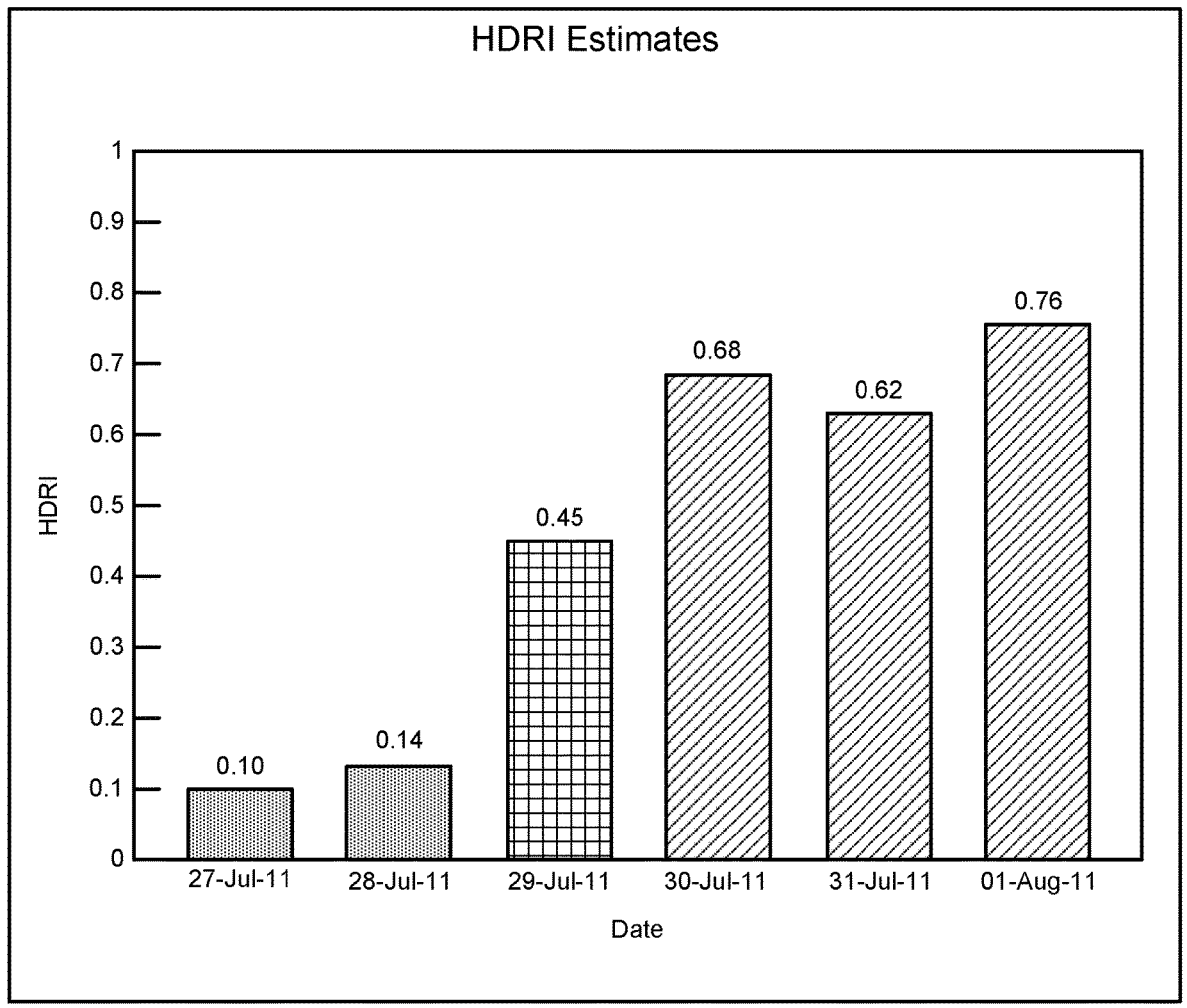
FIG. 13 illustrates measured CRI values for a dengue fever patient in a clinical setting.

In one study, data was collected in Thailand on children that have dengue hemorrhagic fever. The patients were periodically monitored with a NEXFIN continuous non-invasive blood pressure monitor for 10 to 15 min periods each day. Using the NEXFIN signals, the HDRI value was calculated during these monitoring periods. FIG. 13 shows a plot 1300 of HDRI data from one subject. The horizontal axis shows the day and vertical axis shows the estimated HDRI value. The HDRI can clearly be seen tracking resuscitation over a period of 6 days, starting when the patient is the sickest (27 Jul. 2011) and treatment begins, and ending on 1 Aug. 2011 when the patient has shown significant recovery. This patient received a blood transfusion on 29 Jul. 2011.

Figure 14:
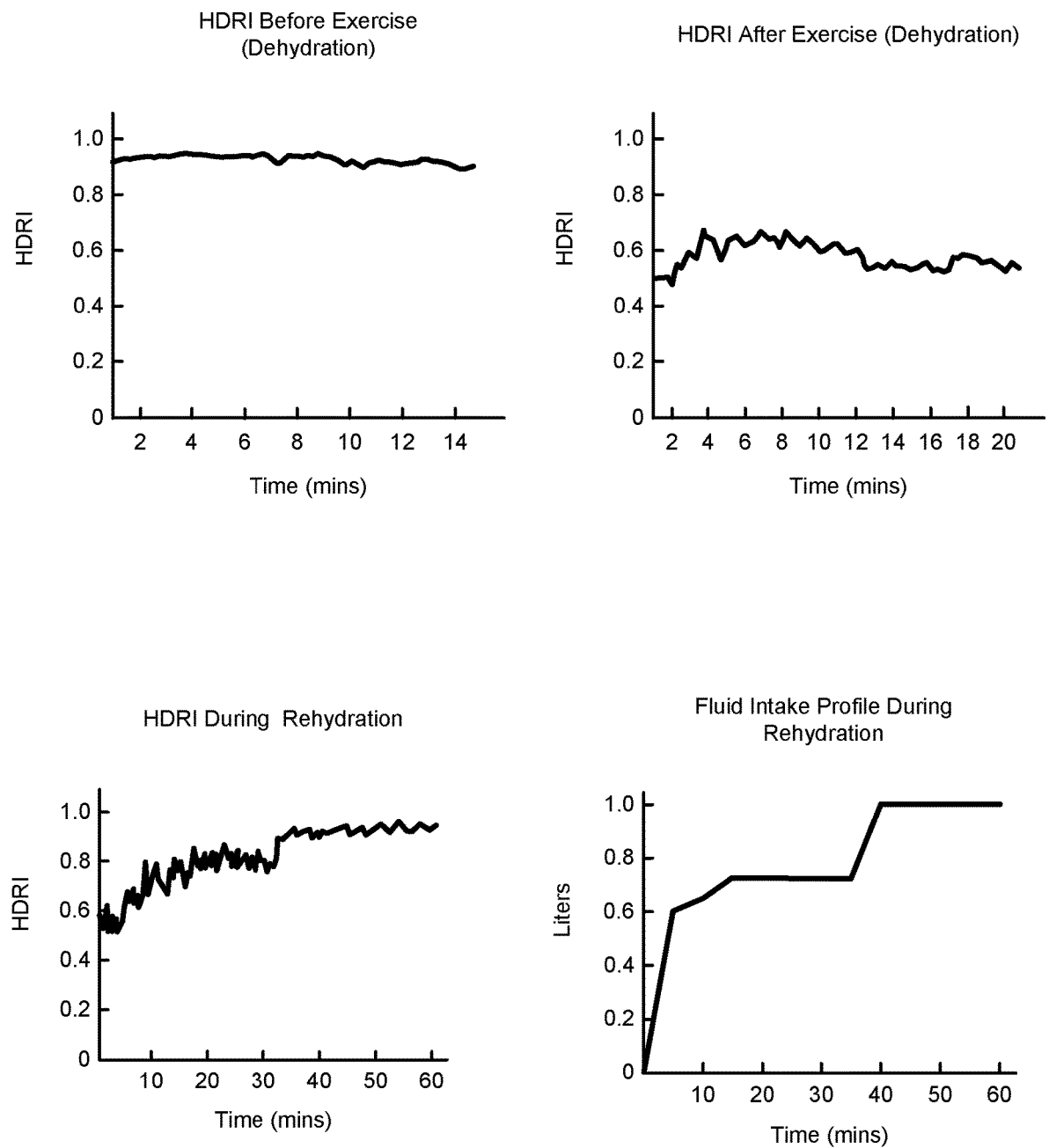
FIG. 14 illustrates measured HDRI values for a test subject undergoing dehydration and rehydration.

In another study, a subject was monitored by a HDRI monitor (including a NONIN OEM III pulse ox sensor) during a dehydration study with the following protocol. The subjected started well hydrated, jogged for 44 minutes, at an ambient temperature of 30 C, and then rehydrated over a 1 hour period. The HDRI profiles for this are shown in FIG. 14. The subject's weight was recorded before exercise, immediately after exercise and after rehydration. The subject lost 0.7 Kg while exercising and increased 0.9 Kg by consuming 1 L of fluids. We assume this 700 g loss represents a 700 ml loss of fluids.

The loss of 700 ml of fluids due to dehydration is clearly observable using HDRI. From the pre-exercise plot 1400 and post-exercise plot 1405, one can see that the subject's HDRI is reduced from about 0.95 to as low as 0.5 after exercise. Note also that the HDRI levels are stable in the pre-exercise plot 1400 and post-exercise plot 1405. We can also see the oral rehydration taking effect in the rehydration plot 1400. After about 35 minute the subject appears fully rehydrated, with an HDRI of about 0.95, similar to the subject's pre-exercise HDRI.

CONCLUSION

This document discloses novel tools and techniques for estimating hemodynamic reserve and similar physiological states. While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system, comprising:
one or more sensors to obtain physiological data from a patient, wherein the physiological data is cardiovascular data of the patient; and
a computer system in communication with the one or more sensors, the computer system comprising:
  one or more processors; and
  a non-transitory computer readable medium in communication with the one or more processors, the non-transitory computer readable medium having encoded thereon a set of instructions executable by the computer system to perform one or more operations, the set of instructions comprising:
    instructions for receiving the physiological data from the one or more sensors;
    instructions for analyzing the physiological data, wherein analyzing the physiological data further comprises:
      comparing the physiological data against a pre-existing model, the pre-existing model comprising a plurality of waveforms of reference data, each waveform of the plurality of waveforms corresponding to a respective hemodynamic reserve index value determined by the following formula:

$$HDRI(t) = 1 - \frac{BLV(t)}{BLV_{HDD}}$$

where HDRI(t) is the hemodynamic reserve at time t, BLV(t) is an intravascular volume loss of the patient at time t, and $BLV_{HDD}$ is an intravascular volume loss of the patient at a point of hemodynamic decompensation, and
      wherein the physiological data includes waveform data of the patient, wherein waveform data of the patient includes one or more patient waveforms, wherein comparing the physiological data against the pre-existing model comprises comparing waveform data of the patient against the plurality of waveforms of reference data, and
      determining a similarity between a respective patient waveform of the one or more patient waveforms and each of one or more waveforms of the plurality of waveforms of reference data individually;

instructions for estimating the hemodynamic reserve index value of the patient, based at least in part on the respective similarities of the respective patient waveform to each of the one or more waveforms of the plurality of waveforms of reference data individually; and instructions for taking one or more actions based on the estimated hemodynamic reserve index value of the patient.

2. A method, comprising:

monitoring, with one or more sensors, physiological data of a patient, wherein the physiological data is cardiovascular data of the patient;

analyzing, with a computer system, the physiological data, wherein analyzing the physiological data further comprises:

comparing the physiological data against a pre-existing model, the pre-existing model comprising a plurality of waveforms of reference data, each waveform of the plurality of waveforms corresponding to a respective hemodynamic reserve index value determined by the following formula:

$$HDRI(t) = 1 - \frac{BLV(t)}{BLV_{HDD}}$$

where HDRI(t) is the hemodynamic reserve at time t, BLV(t) is an intravascular volume loss of the patient at time t, and $BLV_{HDD}$ is an intravascular volume loss of the patient at a point of hemodynamic decompensation, and wherein the physiological data includes waveform data of the patient, wherein waveform data of the patient includes one or more patient waveforms, wherein comparing the physiological data against the pre-existing model comprises comparing waveform data of the patient against the plurality of waveforms of reference data, and determining a similarity between a respective patient waveform of the one or more patient waveforms and each of one or more waveforms of the plurality of waveforms of reference data individually;

estimating, with the computer system, the hemodynamic reserve index value of the patient, based at least in part on respective similarities of the respective patient waveforms to each of the one or more waveforms of the plurality of waveforms of reference data individually; and taking, with the computer system, one or more actions based on the estimated hemodynamic reserve index value of the patient.

3. The method of claim 2, further comprising:
estimating, based on the hemodynamic reserve index value of the patient, a dehydration state of the patient.

4. The method of claim 2, further comprising:
predicting, with the computer system, the hemodynamic reserve index value of the patient at one or more time points in the future, based on the physiological data.

5. The method of claim 2, wherein the estimate of the hemodynamic reserve index value of the patient is based on a fixed time history of monitoring the physiological data of the patient.

6. The method of claim 2, wherein the estimate of the hemodynamic reserve index value of the patient is based on a dynamic time history of monitoring the physiological data of the patient.

7. The method of claim 2, wherein the estimate of the hemodynamic reserve index value of the patient is based on a baseline estimate of the patient's hemodynamic reserve index value established when the patient is euvolemic.

8. The method of claim 2, wherein the estimate of the hemodynamic reserve index value of the patient is not based on a baseline estimate of the patient's hemodynamic reserve index value established when the patient is euvolemic.

9. The method of claim 2, wherein taking one or more actions comprises:
displaying, with a display, the estimated hemodynamic reserve index value of the patient.

10. The method of claim 2, further comprising:
normalizing the estimate of the hemodynamic reserve index value of the patient relative to a first blood volume value corresponding to euvolemia and a second blood volume value corresponding to cardiovascular collapse.

11. The method of claim 10, wherein the first blood volume value corresponding to euvolemia is 1 and the second blood volume value corresponding to cardiovascular collapse is 0.

12. The method of claim 10, wherein taking one or more actions comprises displaying a graphical plot showing the normalized first blood volume value corresponding to euvolemia, the normalized second blood volume value corresponding to cardiovascular collapse, and the normalized estimate of the hemodynamic reserve index value relative to the normalized first blood volume value corresponding to euvolemia and the normalized second blood volume value corresponding to cardiovascular collapse.

13. The method of claim 2, further comprising:
normalizing the estimate of the hemodynamic reserve index value of the patient relative to a first blood volume value corresponding to euvolemia, a second blood volume value corresponding to circulatory overload, and a third blood volume value corresponding to cardiovascular collapse.

14. The method of claim 13, wherein the second blood volume value corresponding to circulatory overload is 1, the first blood volume value corresponding to euvolemia is 0, and the third blood volume value corresponding to cardiovascular collapse is −1.

15. The method of claim 13, wherein the second blood volume value corresponding to circulatory overload is >1, the first blood volume value corresponding to euvolemia is 1, and the third blood volume value corresponding to cardiovascular collapse is 0.

16. The method of claim 13, wherein taking one or more actions comprises:
displaying a graphical plot showing the normalized second blood volume value, the normalized first blood volume value, the normalized third blood volume value, and the normalized estimate of the hemodynamic reserve index value relative to the normalized second blood volume value, the normalized first blood volume value, the normalized third blood volume value.

17. The method of claim 2, wherein taking one or more actions comprises:
determining a probability that the patient is bleeding.

18. The method of claim 2, wherein taking one or more actions comprises:
selecting, with the computer system, a recommended treatment option for the patient.

19. The method of claim 18, further comprising:
displaying, with a display, the recommended treatment option.

20. The method of claim 18, wherein the recommended treatment option is selected from the group consisting of: optimizing hemodynamics of the patient, a ventilator adjustment, an intravenous fluid adjustment, transfusion of blood or blood products to the patient, infusion of volume expanders to the patient, a change in medication administered to the patient, a change in patient position, and surgical therapy.

21. The method of claim 2, further comprising:
repeating the operations of monitoring physiological data of the patient, analyzing the physiological data, and estimating the hemodynamic reserve index value of the patient, to produce a new estimated hemodynamic reserve index value of the patient.

22. The method of claim 2, wherein at least one of the one or more sensors is selected from the group consisting of a blood pressure sensor, an intracranial pressure monitor, a central venous pressure monitoring catheter, an arterial catheter, an electroencephalograph, a cardiac monitor, a transcranial Doppler sensor, a transthoracic impedance plethysmograph, a pulse oximeter, a near infrared spectrometer, a ventilator, an accelerometer, and an electronic stethoscope.

23. The method of claim 2, wherein the one or more types of physiological data comprises blood pressure waveform data.

24. The method of claim 2, wherein the one or more types of physiological data comprises plethysmograph waveform data.

25. The method of claim 2, wherein the one or more types of physiological data comprises photoplethysmograph (PPG) waveform data.

26. The method of claim 2, further comprising:
estimating a first value of the hemodynamic reserve index when the patient is in a first position;
estimating a second value of the hemodynamic reserve index when the patient is in a second position; and
estimating a sensitivity of the patient to volume loss based on a difference between the first value and the second value.

27. The method of claim 26, wherein the first position is selected from the group consisting of lying prone and sitting, and wherein the second position is selected from the group consisting of sitting and standing.

28. The method of claim 2, further comprising:
generating the pre-existing model.

29. The method of claim 28, wherein the plurality of waveforms of reference data is generated by inducing one or more test subjects to enter one or more physiological states, and obtaining physiological data from one or more test subjects while the one or more test subjects is in a respective physiological state of the one or more physiological states.

30. The method of claim 29, further comprising:
inducing the physiological state of reduced circulatory system volume in the one or more test subjects.

31. The method of claim 30, wherein inducing the physiological state comprises subjecting the one or more test subjects to lower body negative pressure ("LBNP").

32. The method of claim 30, wherein inducing the physiological state comprises subjecting the one or more test subjects to dehydration.

33. The method of claim 29, wherein the one or more physiological states comprises a state of cardiovascular collapse.

34. The method of claim 29, wherein the one or more physiological states comprises a state of euvolemia.

35. The method of claim 29, wherein the one or more physiological states comprises a state of hypervolemia.

36. The method of claim 29, wherein the one or more physiological states comprises a state of dehydration.

37. The method of claim 29, further comprising correlating the physiological data of the test subject to the respective physiological state, wherein correlating the physiological data of the one or more test subjects with the physiological state of the one or more test subjects comprises:
identifying a most predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter of the physiological data of the one or more test subjects, and wherein each of the one or more outcomes $o_k$ represents a physiological state measurement of the one or more physiological states respectively;
autonomously learning a set of probabilistic predictive models $\hat{o}_k = M_k(S_k)$, where $\hat{o}_k$ is a prediction of outcome $o_k$ derived from a model $M_k$ that uses as inputs values obtained from the set of signals $S_k$; and
repeating the operation of autonomously learning incrementally from data that contains examples of values of signals $s_1, s_2, \ldots, s_D$ and corresponding outcomes $o_1, o_2, \ldots, o_K$.

38. The method of claim 2, wherein taking one or more actions comprises:
controlling operation of hemodialysis equipment, based at least in part on the estimate of the hemodynamic reserve index value of the patient.

39. The method of claim 38, wherein controlling operation of the hemodialysis equipment comprises adjusting an ultra-filtration rate of the hemodialysis equipment.

40. The method of claim 2, wherein determining the similarity between the respective patient waveform and each of the one or more waveforms of the plurality of waveforms of reference data individually further comprises:
producing one or more similarity coefficients, each similarity coefficient of the one or more similarity coefficients expressing a respective similarity between the respective patient waveform and individual waveforms of the one or more waveforms of the plurality of waveforms of reference data;
wherein estimating the hemodynamic reserve index value of the patient further comprises:
normalizing the one or more similarity coefficients of the one or more waveforms of the plurality of waveforms of reference data;
summing each respective hemodynamic reserve index value, corresponding to a respective individual waveform of the one or more waveforms of the plurality of waveforms of reference data, weighted by the normalized similarity coefficient corresponding to the respective individual waveform of the one or more waveforms of the plurality of waveforms of reference data, for each of the one or more waveforms of the plurality of waveforms of reference data; and
determining, for the respective patient waveform, an estimated hemodynamic reserve index value for the patient based on the sum of the hemoynamic reserve index values as weighted by the normalized similarity coefficients.

41. The method of claim 40, wherein one or more of the plurality of sample waveforms are generated by exposing one or more test subjects to a state of hemodynamic decompensation, or a series of states progressing toward hemodynamic compensation, and monitoring physiological data of the one or more test subjects.

42. An apparatus, comprising: a non-transitory computer readable medium having encoded thereon a set of instructions executable by one or more computers to perform one or more operations, the set of instructions comprising:

instructions for receiving physiological data from one or more sensors, wherein the physiological data is cardiovascular data of the patient;

instructions for analyzing the physiological data, wherein analyzing the physiological data further comprises:

comparing the physiological data against a pre-existing model, the pre-existing model comprising a plurality of waveforms of reference data, each waveform of the plurality of waveforms corresponding to a respective hemodynamic reserve index value determined by the following formula:

$$HDRI(t) = 1 - \frac{BLV(t)}{BLV_{HDD}}$$

where HDRI(t) is the hemodynamic reserve at time t, BLV(t) is an intravascular volume loss of the patient at time t, and $BLV_{HDD}$ is an intravascular volume loss of the patient at a point of hemodynamic decompensation, and wherein the physiological data includes waveform data of the patient, wherein waveform data of the patient includes one or more patient waveforms, wherein comparing the physiological data against the pre-existing model comprises comparing waveform data of the patient against the plurality of waveforms of reference data, and determining a similarity between a respective patient waveform of the one or more patient waveforms and each of one or more waveforms of the plurality of waveforms of reference data individually;

instructions for estimating, with the computer system, a hemodynamic reserve index value of the patient, based at least in part on respective similarities of the respective patient waveform to each of the one or more waveforms of the plurality of waveforms of reference data individually; and instructions for instructions for taking one or more actions based on the estimated hemodynamic reserve index value of the patient.

* * * * *